(12) United States Patent
Stergiou et al.

(10) Patent No.: US 11,058,765 B2
(45) Date of Patent: Jul. 13, 2021

(54) MEANS AND METHODS FOR TREATING HSV

(71) Applicant: REDBIOTEC AG, Schlieren (CH)

(72) Inventors: Garyfalia Stergiou, Zurich (CH); Christian Schaub, Waedenswil (CH); Corinne John, Horgen (CH)

(73) Assignee: REDBIOTEC AG, Schlieren (CH)

( * ) Notice: Subject to any disclaimer, the term of this patent is extended or adjusted under 35 U.S.C. 154(b) by 0 days.

(21) Appl. No.: 16/084,766

(22) PCT Filed: Mar. 14, 2017

(86) PCT No.: PCT/EP2017/056044
§ 371 (c)(1),
(2) Date: Sep. 13, 2018

(87) PCT Pub. No.: WO2017/157969
PCT Pub. Date: Sep. 21, 2017

(65) Prior Publication Data
US 2019/0247492 A1 Aug. 15, 2019

(30) Foreign Application Priority Data

Mar. 14, 2016 (LU) .......................................... 92997
Mar. 14, 2016 (LU) .......................................... 92998
Mar. 14, 2016 (LU) .......................................... 92999

(51) Int. Cl.
| | | |
|---|---|---|
| *A61K 39/245* | (2006.01) | |
| *A61K 9/12* | (2006.01) | |
| *A61P 31/22* | (2006.01) | |
| *C12N 15/85* | (2006.01) | |
| *A61K 39/00* | (2006.01) | |
| *A61K 39/12* | (2006.01) | |

(52) U.S. Cl.
CPC ............ *A61K 39/245* (2013.01); *A61K 39/12* (2013.01); *A61P 31/22* (2018.01); *C12N 15/85* (2013.01); *A61K 2039/70* (2013.01); *C12N 2710/16634* (2013.01)

(58) Field of Classification Search
CPC .. A61K 39/245; A61K 39/12; A61K 2039/70; A61K 2039/58; A61P 31/22; C12N 15/85; C12N 2710/16634
See application file for complete search history.

(56) References Cited

U.S. PATENT DOCUMENTS

2003/0190324 A1* 10/2003 Koelle ..................... A61P 31/22
424/186.1
2013/0224236 A1* 8/2013 Koelle ..................... A61K 39/12
424/186.1

OTHER PUBLICATIONS

Colgrove R, Diaz F, Newman R, Saif S, Shea T, Young S, Henn M, Knipe DM. Genomic sequences of a low passage herpes simplex virus 2 clinical isolate and its plaque-purified derivative strain. Virology. Feb. 2014;450-451:140-5. Epub Dec. 31, 2013.*
Koelle DM, Dong L, Byrd B, Liu C. Marshak JO. Viral protein 22 [Human alphaherpesvirus 2], GenBank: ADE87566.1, Dep. Apr. 14, 2010.*
Adamiak B, Ekblad M, Bergstrom T, Ferro V, Trybala E.Glycoprotein E [Human alphaherpesvirus 2], GenBank: ABU45436.1. Dep. Nov. 29, 2007.*
Petro CD, Gonzalez PA, Weiss K, Khajoueinejad N, Cheshenko N, Weinrick BC, Sengupta M, Jacobs WR, Herold BC. Envelope glycoprotein E [Human herpesvirus 2], GenBank: AMB66387.1. Dep. Feb. 6, 2016.*
Colgrove R, et. al. Apr. 30, 2014. Myristylated tegument protein [Human alphaherpesvirus 2] GenBank: AHG54674.1.*
Colgrove R, et. al. Apr. 30, 2014. tegument protein UL16 [Human alphaherpesvirus 2] GenBank: AHG54679.1.*
Colgrove R, et. al. Apr. 30, 2014. tegument protein UL21 [Human alphaherpesvirus 2] GenBank: AHG54684.1.*
Colgrove R, et. al. Apr. 30, 2014. transactivating tegument protein VP16 [Human alphaherpesvirus 2] GenBank: AHG54712.1.*
Colgrove R, et. al. Apr. 30, 2014. nuclear egress membrane protein [Human alphaherpesvirus 2] GenBank: AHG54698.1.*
Colgrove R, et. al. Apr. 30, 2014. nuclear egress lamina protein [Human alphaherpesvirus 2] GenBank: AHG54695.1.*
Vittone V, Diefenbach E, Triffett D, Douglas MW, Cunningham AL, Diefenbach RJ. Determination of interactions between tegument proteins of herpes simplex virus type 1. J Virol. Aug. 2005;79(15):9566-71.*
Marconi P, Argnani R, Epstein AL, Manservigi R. HSV as a Vector in Vaccine Development and Gene Therapy. In: Madame Curie Bioscience Database [Internet]. Austin (TX): Landes Bioscience; 2000-2013. Available from: https://www.ncbi.nlm.nih.gov/books/NBK7024/.*
Harper AL, Meckes DG Jr, Marsh JA, Ward MD, Yeh PC, Baird NL, Wilson CB, Semmes OJ, Wills JW. Interaction domains of the UL16 and UL21 tegument proteins of herpes simplex virus. J Virol. Mar. 2010;84(6):2963-71. Epub Dec. 30, 2009.*
Han J, Chadha P, Starkey JL, Wills JW. Function of glycoprotein E of herpes simplex virus requires coordinated assembly of three tegument proteins on its cytoplasmic tail. Proc Natl Acad Sci USA. Nov. 27, 2012;109(48):19798-803. Epub Nov. 12, 2012.*
Chadha P, Han J, Starkey JL, Wills JW. Regulated interaction of tegument proteins UL16 and UL11 from herpes simplex virus. J Virol. Nov. 2012;86(21):11886-98. doi: 10.1128/JVI.01879-12. Epub Aug. 22, 2012.*
Dropulic LK, Cohen JI. The challenge of developing a herpes simplex virus 2 vaccine. Expert Rev Vaccines. Dec. 2012;11(12):1429-40. doi: 10.1586/erv.12.129. Review.*

(Continued)

*Primary Examiner* — Rachel B Gill
(74) *Attorney, Agent, or Firm* — Seed IP Law Group LLP

(57) ABSTRACT

The present invention relates to a vaccine composition comprising a multimeric complex of Herpes Simplex Virus (HSV) polypeptides for the treatment or vaccination against HSV. The present invention also relates to a vector comprising a polynucleotide encoding the HSV polypeptides and a host cell comprising the vector. The present invention further comprises a method for producing the vaccine composition.

19 Claims, 16 Drawing Sheets

Specification includes a Sequence Listing.

(56) References Cited

OTHER PUBLICATIONS

Long D, Skoberne M, Gierahn TM, Larson S, Price JA, Clemens V, Baccari AE, Cohane KP, Garvie D, Siber GR, Flechtner JB. Identification of novel virus-specific antigens by CD4+and CD8+T cells from asymptomatic HSV-2 seropositive and seronegative donors. Virology. Sep. 2014;464-465:296-311. Epub Aug. 9, 2014.*
Han J, Chadha P, Starkey JL, Wills JW. Function of glycoprotein E of herpes simplex virus requires coordinated assembly of three tegument proteins on its cytoplasmic tail. Proc Natl Acad Sci USA. Nov. 27, 2012;109(48):19798-803. doi: 10.1073/pnas.1212900109. Epub Nov. 12, 2012. PMID: 23150560; PMCID: PMC3511771.*
Kalantari-Dehaghi M, Chun S, Chentoufi AA, Pablo J, Liang L, Dasgupta G, et. al. Discovery of potential diagnostic and vaccine antigens in herpes simplex virus 1 and 2 by proteome-wide antibody profiling. J Virol. Apr. 2012;86(8):4328-39. Epub Feb. 8, 2012.*
Han J, Chadha P, Meckes DG Jr, Baird NL, Wills JW. Interaction and interdependent packaging of tegument protein UL11 and glycoprotein e of herpes simplex virus. J Virol. Sep. 2011;85(18):9437-46. Epub Jul. 6, 2011.*
Maringer K, Stylianou J, Elliott G. A network of protein interactions around the herpes simplex virus tegument protein VP22. J Virol. Dec. 2012;86(23):12971-82. doi: 10.1128/JVI.01913-12. Epub Sep. 19, 2012. PMID: 22993164; PMCID: PMC3497626.*
McVoy MA. Cytomegalovirus vaccines. Clin Infect Dis. Dec. 2013;57 Suppl 4(Suppl 4):S 196-9.*
Vittone V, Diefenbach E, Triffett D, Douglas MW, Cunningham AL, Diefenbach RJ. Determination of interactions between tegument proteins of herpes simplex virus type 1. J Virol. Aug. 2005;79(15):9566-71. (Year: 2005).*
Chaplin, Enzyme Technology "Ultrasonic cell disruption," http://www1.lsbu.ac.uk/water/enztech/ultrasonic.html (1 page) (Aug. 6, 2014).
Coleman et al., "Recent advances in vaccine development for herpes simplex virus types I and II," *Human Vaccines & Immunotherapeutics* 9(4):729-735 (Apr. 2013).
Elliott et al., "VP16 Interacts via Its Activation Domain with VP22, a Tegument Protein of Herpes Simplex Virus, and Is Relocated to a Novel Macromolecular Assembly in Coexpressing Cells," *Journal of Virology* 69(12):7932-7941 (Dec. 1995).
Guan et al., "HSV-1 nucleocapsid egress mediated by UL31 in association with UL34 is impeded by cellular transmembrane protein 140," *Virology* 464-465:1-10 (2014).

Han et al., "Function of glycoprotein E of herpes simplex virus requires coordinated assembly of three tegument proteins on its cytoplasmic tail," *PNAS* 109(48):19798-19803 (Nov. 27, 2012).
Harper et al., "Interaction Domains of the UL16 and UL21 Tegument Proteins of Herpes Simplex Virus," *Journal of Virology* 84(6):2963-2971 (Mar. 2010).
Koelle et al., "Recognition of Herpes Simplex Virus Type 2 Tegument Proteins by CD4 T Cells Infiltrating Human Genital Herpes Lesions," *Journal of Virology* 72(9):7476-7483 (Sep. 1998).
Morello et al., "Immunization with Herpes Simplex Virus 2 (HSV-2) Genes plus Inactivated HSV-2 is Highly Protective against Acute and Recurrent HSV-2 Disease," *Journal of Virology* 85(7):3461-3472 (Apr. 2011).
Morello et al., "Inactivated HSV-2 in MPL/alum adjuvant provides nearly complete protection against genital infection and shedding following long term challenge and rechallenge," *Vaccine* 30:6541-6550 (2012).
Muller et al., "Herpes simplex virus type 2 tegument proteins contain subdominant T-cell epitopes detectable in BALB/c mice after DNA immunization and infection," *Journal of General Virology* 90:1153-1163 (2009).
O'Regan et al., "Virion incorporation of the herpes simplex virus 1 tegument protein VP22 is facilitated by *trans*-Golgi network localization and is independent of interaction with glycoprotein E," *Virology* 405:176-192 (2010).
Orlando, "Mapping chromosomal proteins in vivo by formaldehyde-crosslinked-chromatin immunoprecipitation," *TIBS* 25:99-104 (Mar. 2000).
Schnee et al., "Common and Specific Properties of Herpesvirus UL34/UL31 Protein Family Members Revealed by Protein Complementation Assay," *Journal of Virology* 80(23):11658-11666 (Dec. 2006).
Saá et al., "Cyclic Amplifcation of Protein Misfolding and Aggregation," *Methods in Molecular Biology vol. 299: Amyloid Proteins: Methods and Protocols*, Edited by E. M. Sigurdsson, Humana Press Inc., Totowa, NJ (pp. 58-59) (7 pages) (2005).
Skoberne et al., "An Adjuvanted Herpes Simplex Virus 2 Subunit Vaccine Elicits a T Cell Response in Mice and Is an Effective Therapeutic Vaccine in Guinea Pigs," *Journal of Virology* 87(7):3930-3942 (Apr. 2013).
Tainer, "Dose sonication affect protein-protein interaction during protein extraction?" https://www.researchgate.net/post/_sonication_affect_protein-protein-interaction_during_protein_extraction (2 pages) (Mar. 4, 2018).

* cited by examiner

FIGURE 1

UL11 protein of HSV-2
MGLAFSGARPCCCRHNVIITDGGEVVSLTAHEFDVVDIESEEEGNFYVPPDMRVVTRAPGPQYRRASD
PPSRHTRRRDPDVARPPATLTPPLSDSE
(SEQ ID NO: 1)

UL16 protein of HSV-2
MAQRALWRPQATPGPPGAAAPPGHRGAPPDARAPDPGPEADLVARIANSVFVWRVVRGDERLKIFR
CLTVLTEPLCQVALPDPDPERALFCEIFLYLTRPKALRLPSNTFFAIFFFNRERRYCATVHLRSVTHPRT
PLLCTLAFGHLEAASPPEETPDPAAEQLADEPVAHELDGAYLVPTEPPPNPGACCALGPGAWWHLPG
GRIYCWAMDDDLGSLCPPGSRARHLGWLLSRITDPPGGGGACAPTAHIDSANALWRAPAVAEACPCV
APCMWSNMAQRTLAVRGDASLCQLLFGHPVDAVILRQATRRPRITAHLHEVVVGRDGAESVIRPTSAG
WRLCVLSSYTSRLFATSCPAVARAVARASSSDYK
(SEQ ID NO: 2)

UL21 protein of HSV-2
MELSYATTLHHRDVVFYVTADRNRAYFVCGGSVYSVGRPRDSQPGEIAKFGLVVRGTGPKDRMVANY
VRSELRQRGLRDVRPVGEDEVFLDSVCLLNPNVSSERDVINTNDVEVLDECLAEYCTSLRTSPGVLVT
GVRVRARDRVIELFEHPAIVNISSRFAYTPSPYVFALAQAHLPRLPSSLEPLVSGLFDGIPAPRQPLDAR
DRRTDVVITGTRAPRPMAGTGAGGAGAKRATVSEFVQVKHIDRVVSPSVSSAPPPSAPDASLPPPGL
QEAAPPGPPLRELVWVFYAGDRALEEPHAESGLTREEVRAVHGFREQAWKLFGSVGAPRAFLGAAL
ALSPTQKLAVYYYLIHRERRMSPFPALVRLVGRYIQRHGLYVPAPDEPTLADAMNGLFRDALAAGTVAE
QLLMFDLLPPKDVPVGSDARADSAALLRFVDSQRLTPGGSVSPEHVMYLGAFLGVLYAGHGRLAAAT
HTARLTGVTSLVLTVGDVDRMSAFDRGPAGAAGRTRTAGYLDALLTVCLARAQHGQSV
(SEQ ID NO: 3)

gE protein of HSV-2
MARGAGLVFFVGVWVVSCLAAAPRTSWKRVTSGEDVVLLPAPAGPEERTRAHKLLWAAEPLDACGPL
RPSWVALWPPRRVLETVVDAACMRAPEPLAIAYSPPFPAGDEGLYSELAWRDRVAVVNESLVIYGALE
TDSGLYTLSVVGLSDEARQVASVVLVVEPAPVPTPTPDDYDEEDDAGVSERTPVSVPPPTPPRRPPVA
PPTHPRVIPEVSHVRGVTVHMETPEAILFAPGETFGTNVSIHAIAHDDGPYAMDVVWMRFDVPSSCAE
MRIYEACLYHPQLPECLSPADAPCAVSSWAYRLAVRSYAGCSRTTPPPRCFAEARMEPVPGLAWLAS
TVNLEFQHASPQHAGLYLCVVYVDDHIHAWGHMTISTAAQYRNAVVEQHLPQRQPEPVEPTRPHVRA
PPPAPSARGPLRLGAVLGAALLLAALGLSAWACMTCWRRRSWRAVKSRASATGPTYIRVADSELYAD
WSSDSEGERDGSLWQDPPERPDSPSTNGSGFEILSPTAPSVYPHSEGRKSRRPLTTFGSGSPGRRH
SQASYSSVLW
(SEQ ID NO: 4)

FIGURE 1 (continued)

Cytoplasmic tail of gE protein of HSV-2
RRRSWRAVKSRASATGPTYIRVADSELYADWSSDSEGERDGSLWQDPPERPDSPSTNGSGFEILSPT
APSVYPHSEGRKSRRPLTTFGSGSPGRRHSQASYSSVLW
(SEQ ID NO: 5)

UL48 protein of HSV-2

MDLLVDDLFADADGVSPPPPPRPAGGPKNTPAAPPLYATGRLSQAQLMPSPPMPVPPAALFNRLLDDL
GFSAGPALCTMLDTWNEDLFSGFPTNADMYRECKFLSTLPSDVIDWGDAHVPERSPIDIRAHGDVAFP
TLPATRDELPSYYEAMAQFFRGELRAREESYRTVLANFCSALYRYLRASVRQLHRQAHMRGRNRDLR
EMLRTTIADRYYRETARLARVLFLHLYLFLSREILWAAYAEQMMRPDLFDGLCCDLESWRQLACLFQPL
MFINGSLTVRGVPVEARRLRELNHIREHLNLPLVRSAAAEEPGAPLTTPPVLQGNQARSSGYFMLLIRA
KLDSYSSVATSEGESVMREHAYSRGRTRNNYGSTIEGLLDLPDDDDAPAEAGLVAPRMSFLSAGQRP
RRLSTTAPITDVSLGDELRLDGEEVDMTPADALDDFDLEMLGDVESPSPGMTHDPVSYGALDVDDFEF
EQMFTDAMGIDDFGG
(SEQ ID NO: 6)

UL49 protein of HSV-2

MTSRRSVKSCPREAPRGTHEELYYGPVSPADPESPRDDFRRGAGPMRARPRGEVRFLHYDEAGYAL
YRDSSSSEDNDESRDTARPRRSASVAGSHGPGPARAPPPPGGPVGAGGRSHAPPARTPKMTRGAP
KAPATPATDPARGRRPAQADSAVLLDAPAPTASGRTKTPAQGLAKKLHFSTAPPSPTAPWTPRVAGF
NKRVFCAAVGRLAATHARLAAVQLWDMSRPHTDEDLNELLDLTTIRVTVCEGKNLLQRANELVNPDAA
QDVDATAAARGRPAGRAAATARAPARSASRPRRPLE
(SEQ ID NO: 7)

UL31 protein of HSV-2
MYDIAPRRSGSRPGPGRDKTRRRSRFSAAGNPGVERRASRKSLPSHARRLELCLHERRRYRGFFAAL
AQTPSEEIAIVRSLSVPLVKTTPVSLPFSLDQTVADNCLTLSGMGYYLGIGGCCPACSAGDGRLATVSR
EALILAFVQQINTIFEHRTFLASLVVLADRHSTPLQDLLADTLGQPELFFVHTILRGGGACDPRFLFYPDP
TYGGHMLYVIFPGTSAHLHYRLIDRMLTACPGYRFAAHVWQSTFVLVVRRNAEKPADAEIPTVSAADIY
CKMRDISFDGGLMLEYQRLYATFDEFPPP
(SEQ ID NO: 8)

UL34 protein of HSV-2
MAGMGKPYGGRPGDAFEGLVQRIRLIVPTTLRGGGGESGPYSPSNPPSRCAFQFHGQDGSDEAFPIE
YVLRLMNDWADVPCNPYLRVQNTGVSVLFQGFFNRPHGAPGGAITAEQTNVILHSTETTGLSLGDLDD
VKGRLGLDARPMMASMWISCFVRMPRVQLAFRFMGPEDAVRTRRILCRAAEQALARRRRSRRSQDD
YGAVAVAAAHHSSGAPGPGVAASGPPAPPGRGPARPWHQAVQLFRAPRP
(SEQ ID NO: 9)

Polypeptid linker and 8 His-tag
GAGSGGGGSGGGGSHHHHHHHH
(SEQ ID NO: 10)

FIGURE 2
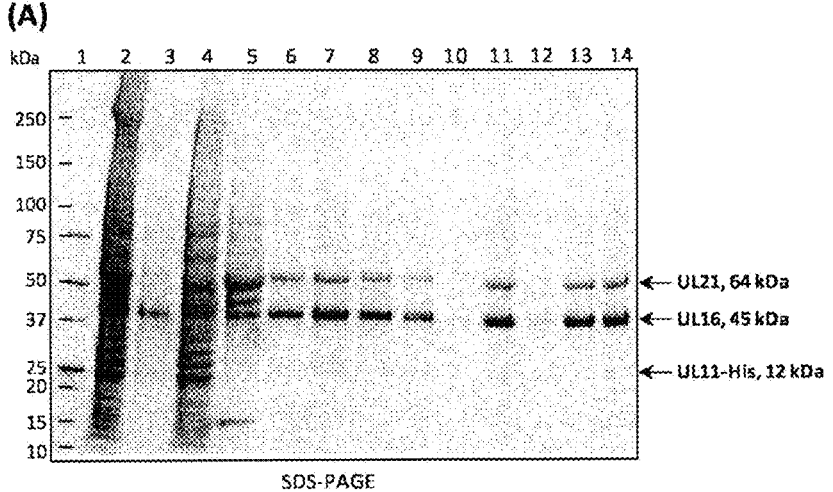
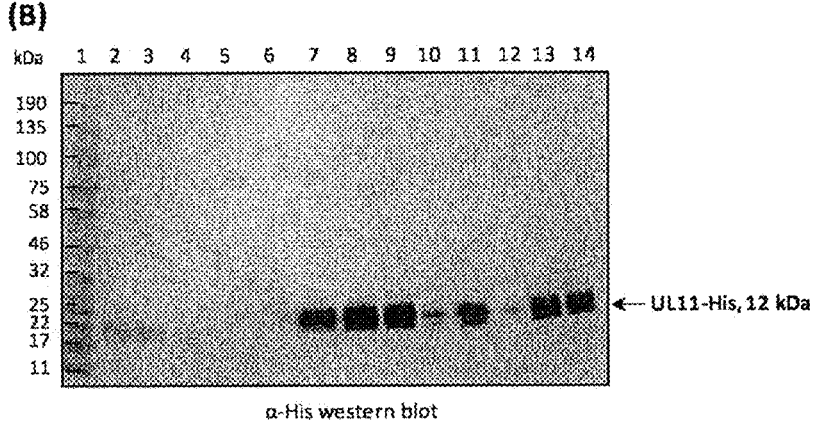

FIGURE 3
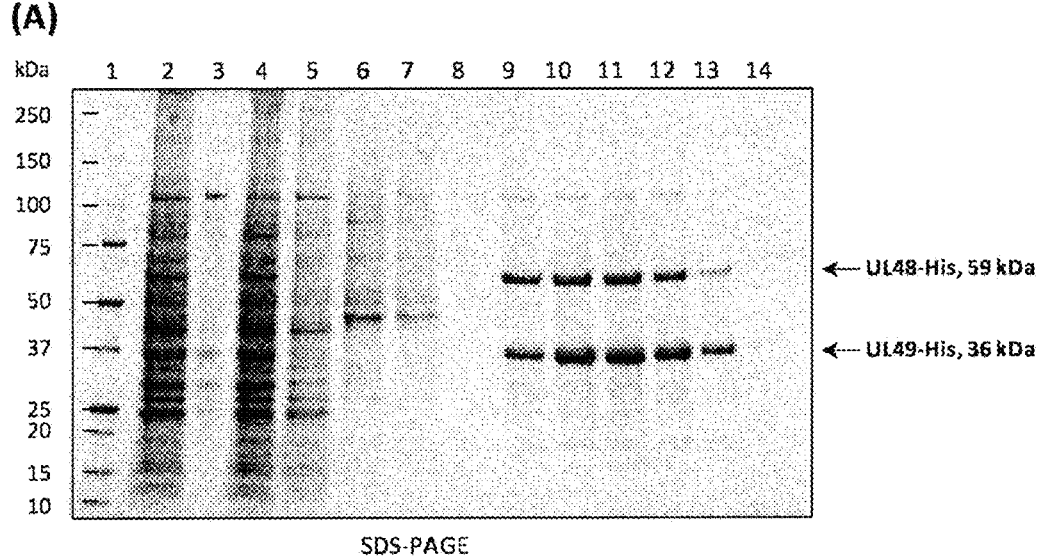
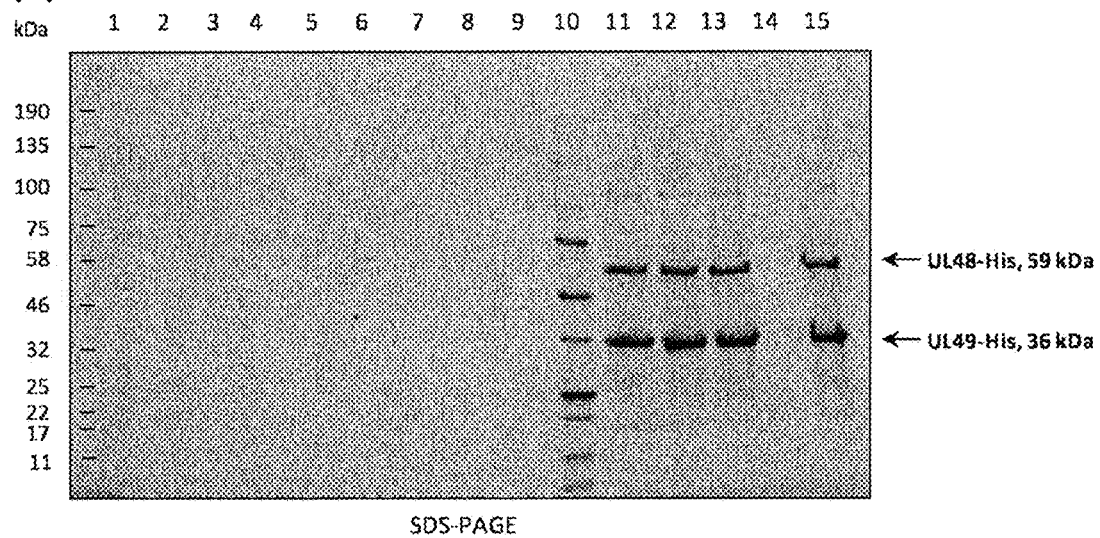

FIGURE 4
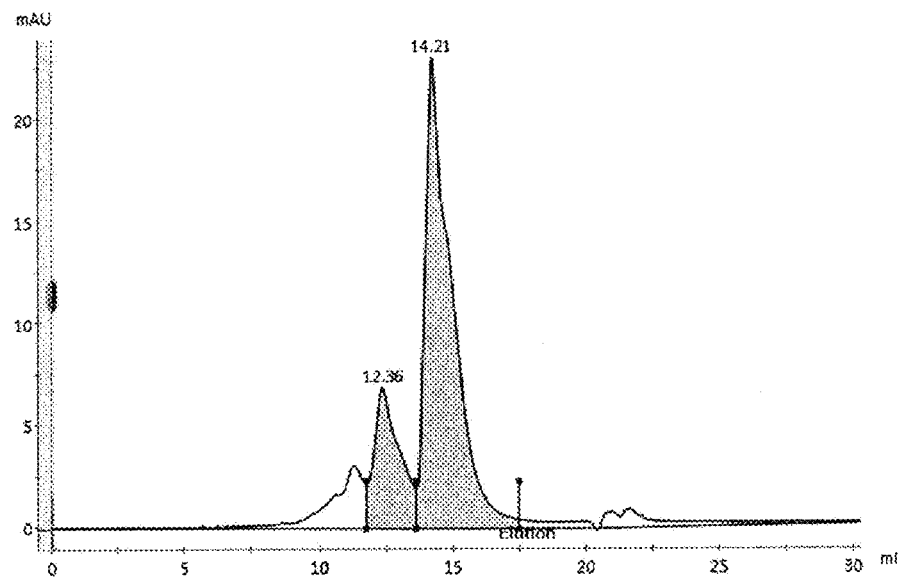
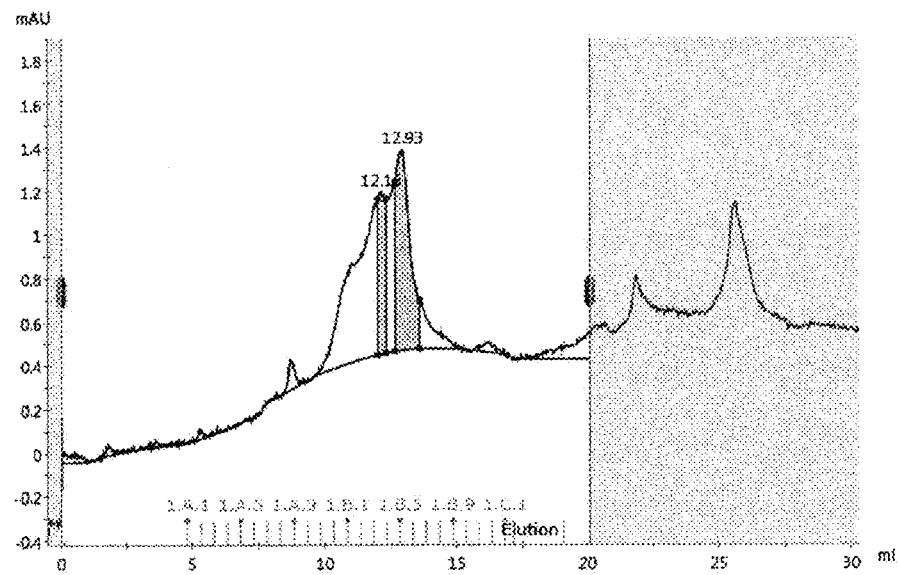

FIGURE 5
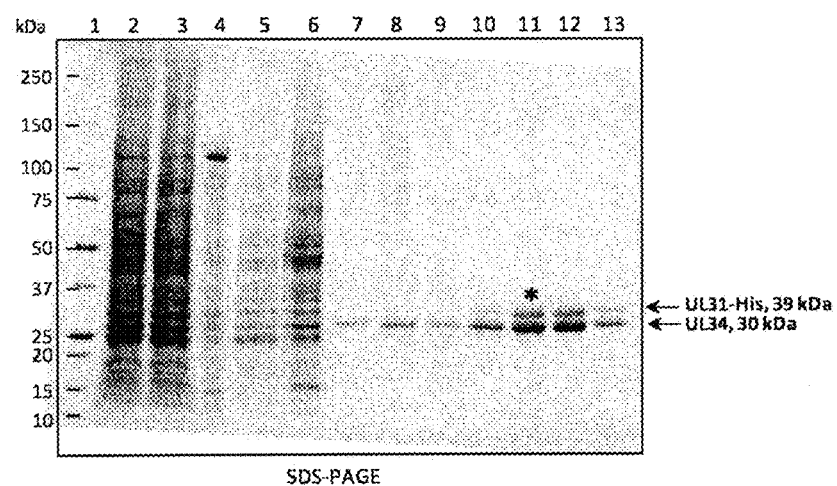
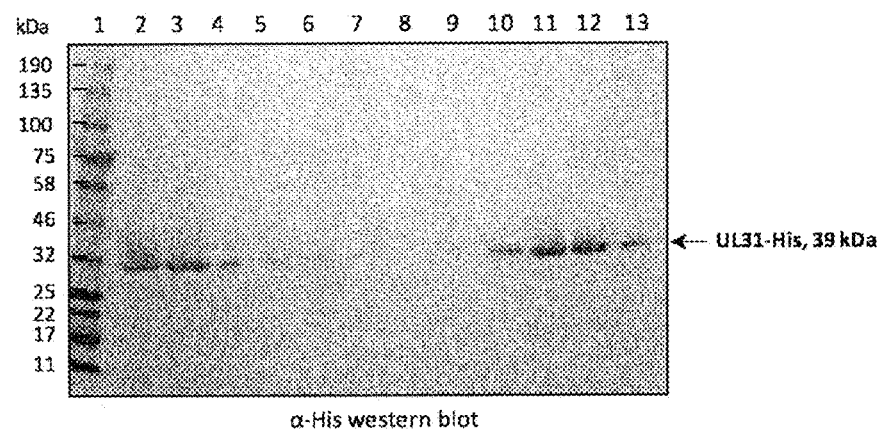

FIGURE 6
(A)
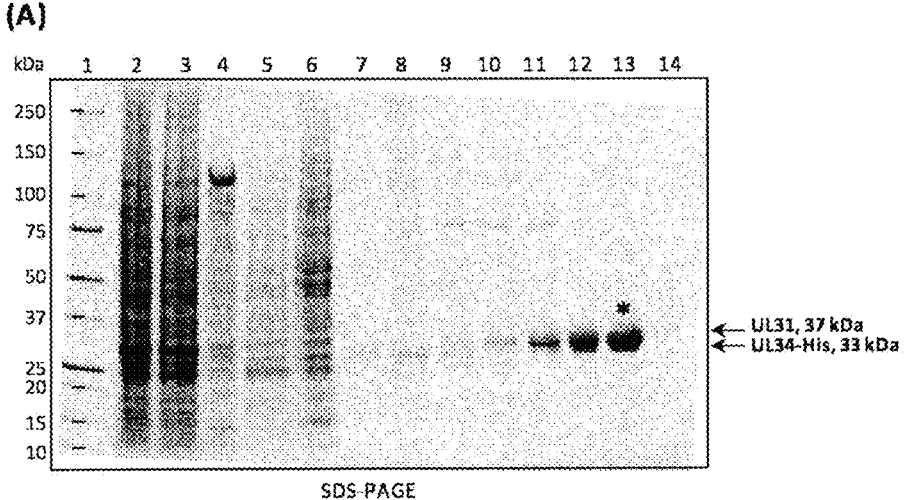
SDS-PAGE
(B)
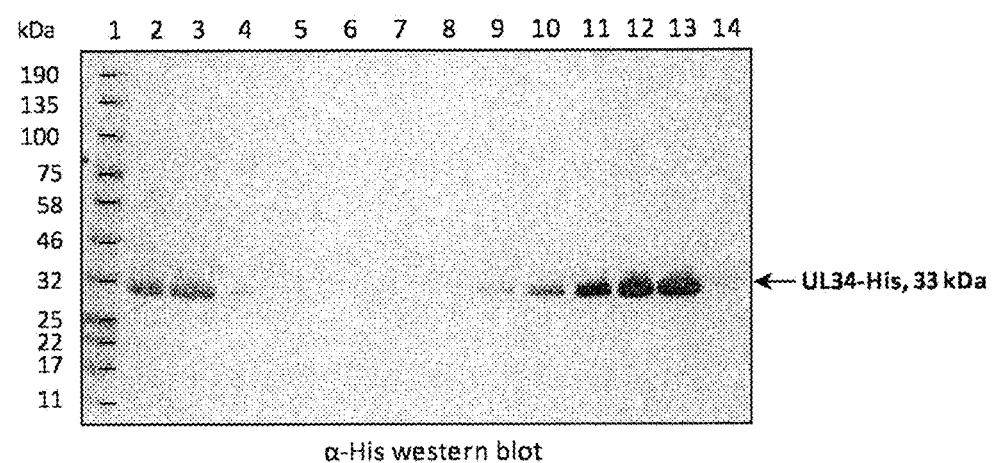
α-His western blot

FIGURE 7
(A)
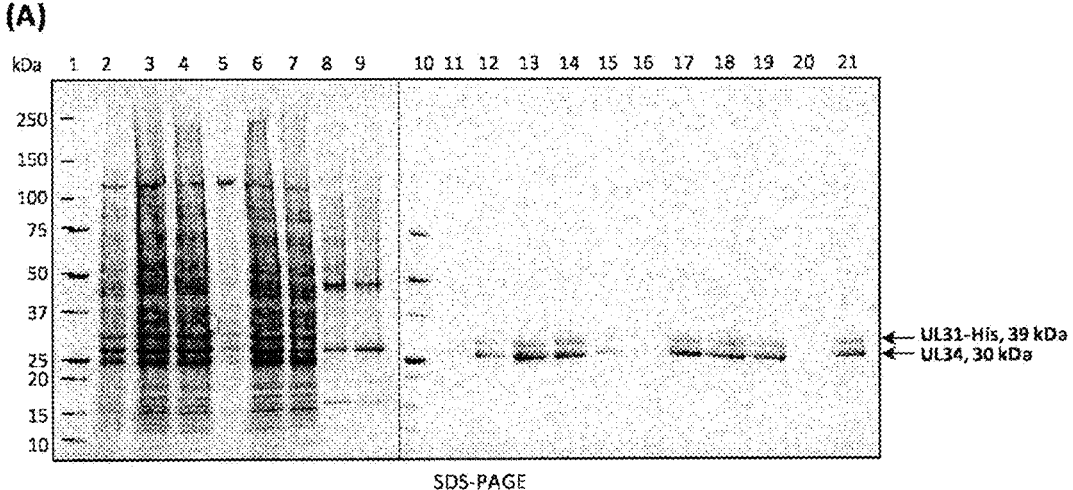
SDS-PAGE
(B)
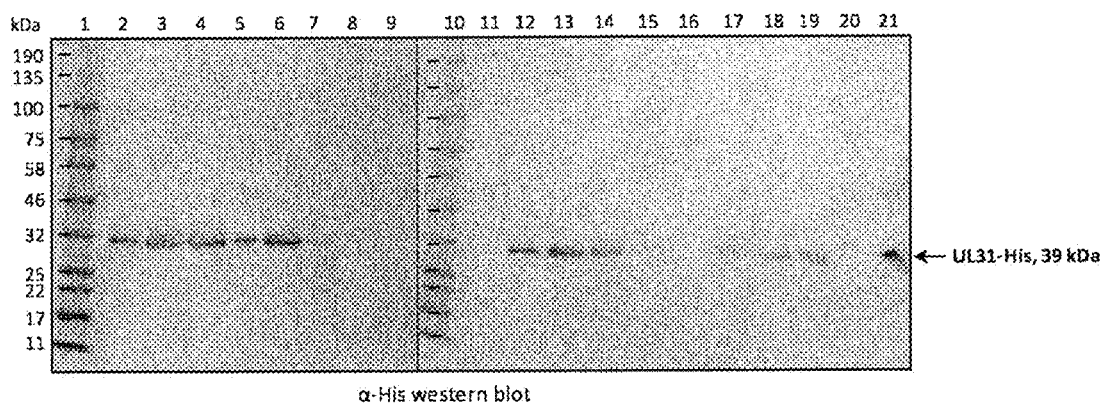
α-His western blot

MEANS AND METHODS FOR TREATING HSV

STATEMENT REGARDING SEQUENCE LISTING

The Sequence Listing associated with this application is provided in text format in lieu of a paper copy, and is hereby incorporated by reference into the specification. The name of the text file containing the Sequence Listing is 790143_401USPC_SEQUENCE_LISTING.txt. The text file is 26.7 KB, was created on Sep. 11, 2018, and is being submitted electronically via EFS-Web.

FIELD OF INVENTION

The present invention relates to a vaccine composition comprising a multimeric complex of Herpes Simplex Virus (HSV) polypeptides for the treatment or vaccination against HSV. The present invention also relates to a vector comprising a polynucleotide encoding the HSV polypeptides and a host cell comprising the vector. The present invention further comprises a method for producing the vaccine composition.

BACKGROUND

Herpes simplex virus is a viral genus of the viral family known as Herpesviridae. The species that infect humans are commonly known as Herpes simplex virus 1 (HSV-1) and Herpes simplex virus 2 (HSV-2), wherein their formal names are Human herpesvirus 1 (HHV-1) and Human herpesvirus 2 (HHV-2), respectively. The initial infection with HSV-1 typically occurs during childhood or adolescence and persists lifelong. Infection rates with HSV-1 are between 40% and 80% worldwide, being higher among people of lower socialeconomic status. In many cases people exposed to HSV-1 demonstrate asymptomatic seroconversion. However, initial infection can also be severe, causing widespread 1 to 2 mm blisters associated with severe discomfort that interferes with eating and drinking to the point of dehydration, last 10 to 14 days, and occur 1 to 26 days after inoculation. Recurrent labial herpes affects roughly one third of the US population, and these patients typically experience 1 to 6 episodes per year. Papules on an erythematous base become vesicles within hours and subsequently progress through ulcerated, crusted, and healing stages within 72 to 96 hours (Cernik et al., 2008, Arch Intern Med., vol. 168, pp. 1137-1144). Global estimates in 2003 assume that 16.2% of the population are infected with HSV-2, being the major cause of genital herpes. The ability of the virus to successfully avoid clearance by the immune system by entering a non-replicating state known as latency leads to lifelong infection. Periodic reactivation from latency is possible and leads to viral shedding from the site of the initial infection. Genital lesions due to herpes are often very painful, and can lead to substantial psychological morbidity. The virus can also be passed from mother to child during birth. Without treatment, 80% of infants with disseminated disease die, and those who do survive are often brain damaged. In addition, genital herpes is associated with an increased risk of HIV acquisition by two- to threefold, HIV transmission on a per-sexual act basis by up to fivefold, and may account for 40-60% of new HIV infections in high HSV-2 prevalence populations (Looker et al., 2008, Bulletin of the World Health Organization, vol. 86, pp. 805-812).

Currently, acyclovir, a synthetic acyclic purine-nucleoside analogue, is the standard therapy for HSV infections and has greatly helped control symptoms. Precursor drugs, valacyclovir (converted to acyclovir) and famciclovir (converted to penciclovir), have been licensed and have better oral bioavailability than acyclovir and penciclovir, respectively. The available drugs have an excellent margin of safety because they are converted by viral thymidine kinase to the active drug only inside virally infected cells. However, HSV can develop resistance to acyclovir through mutations in the viral gene that encodes thymidine kinase by generation of thymidine-kinase-deficient mutants or by selection of mutants with a thymidine kinase unable to phosphorylate acyclovir. Most clinical HSV isolates resistant to acyclovir are deficient in thymidine kinase, although altered DNA polymerase has been detected in some. As HSV can lie latent in neurons for months or years before becoming active, such a therapy may be used to treat symptoms caused by HSV but cannot avoid the periodic reactivation of the virus.

Accordingly, the most effective and economical way to fight HSV would be a vaccine preventing initial infection and/or periodic reactivation of the virus. A lot of effort has been put in the development of such a vaccine in the past several decades. However, attempts to develop a potent HSV vaccine have focused on a limited number of antigens that have shown poor performance in clinical trials. Accordingly, there is an urgent need of a vaccine against HSV.

DETAILED DESCRIPTION

Vaccine Composition

The present invention addresses this need and provides novel vaccine compositions comprising a multimeric complex of Herpes Simplex Virus (HSV) polypeptides UL11, UL16 and UL21, a multimeric complex of Herpes Simplex Virus (HSV) polypeptides UL48, UL49 and gE or a multimeric complex of Herpes Simplex Virus (HSV) polypeptides UL31 and UL34.

The terms "multimeric complex" or "complex" are used interchangeably herein and refer to a stable polypeptide complex composed of at least two polypeptide subunits along with any covalently attached molecules (such as lipid anchors or oligosaccharide) or non-protein prosthetic groups (such as nucleotides or metal ions). Prosthetic group in this context refers to a tightly bound cofactor. Accordingly, a multimeric complex may comprise two polypeptides (i.e. a dimer), three polypeptides (i.e. a trimer) or four polypeptides (i.e. a tetramer). A multimeric complex of the invention relates to a set of interacting proteins that has been shown to exist as a functional unit in vivo and the polypeptides of the multimeric complex of the invention can be co-purified using stringent protein purification methods. Such stringent protein purification methods make use of buffers and solutions that do not force unspecific and/or artificial protein interaction and thus result only in the purification of complexes that stay intact (i.e. no polypeptide of the complex is released) when subjected to stringent wash conditions. Therefore, methods that merely show an interaction of polypeptides, such as immunoprecipitation or pull-down experiments from cell extracts are not considered as suitable methods for purifying a complex of the invention. Likewise, methods that merely show the co-localization of polypeptides or the interaction of polypeptides are not indicative of a complex of the invention, in particular if such a method employs artificially modified polypeptides, such as e.g. yeast-2-hybrid systems. Accordingly, after purification a complex of the invention can be detected using a suitable method (e.g. size exclusion chromatography). Consequently, the mere presence of two or more polypeptides, which may have been shown to exist as a complex in vivo, in a composition are not considered as a complex of the invention as such a complex may form only using specific purification methods and conditions and may only be stable after purification under specific storage conditions. Thus, even if certain polypeptides have been shown to form a complex in vivo, said polypeptides may be present in solution as monomers. In one embodiment the multimeric complex is a dimer comprising HSV polypeptides UL11 and UL16. In a further embodiment the complex is a dimer comprising HSV polypeptides UL16 and UL21. In a preferred embodiment the complex is a trimer comprising HSV polypeptides UL11, UL16 and UL21. In a further preferred embodiment the multimeric complex is a trimer and comprises or consists of HSV polypeptides UL11, UL16 and UL21. In one embodiment the multimeric complex is a dimer comprising HSV polypeptides UL48 and UL49. In a further embodiment the complex is a dimer comprising HSV polypeptides UL49 and gE. In a preferred embodiment the complex is a trimer comprising HSV polypeptides UL48, UL49 and gE. In a further preferred embodiment the multimeric complex is a trimer and comprises or consists of HSV polypeptides UL48, UL49 and gE. In a further preferred embodiment the complex is a dimer comprising or consisting of HSV polypeptides UL31 and UL34. In the multimeric complex of the invention, one or more of the proteins may comprise additional B- and/or T-cell epitopes. Said T-cell epitope can be a CD4 T-cell epitope or a CD8 T-cell epitope. Preferably, a complex of the present invention provides a synergistic effect. Accordingly, a complex of the present invention is preferably capable of eliciting a stronger immune response in an ELISPOT assay with patient PBMC compared to the single proteins.

A complex of the present invention may be generated using suitable means and methods known in the art. A complex of the present invention can be generated by co-expressing the single polypeptides of the complex in a host cell, such that the complex forms in the host cell. A complex of the present invention can also be generated by expressing the single polypeptides of the complex in separate host cells, purifying the single polypeptides from the host cells and admixing the single polypeptides in vitro under conditions allowing formation of the complex. However, a complex of the present invention may also be generated by expressing the single polypeptides of the complex in separate host cells, purifying the single polypeptides from the host cells and administering the single polypeptides to a subject such that the complex forms in vivo. Whether a complex forms in vivo after administering the single polypeptides of the complex to a subject can be determined in a model system, resembling the conditions in vivo (i.e. 37° C., blood, blood serum and physiological salt concentration).

The polypeptides of the vaccine composition may comprise a tag. A polypeptide tag as used herein is an amino acid sequence genetically fused with the recombinant polypeptide, conferring purification and/or detection of the polypeptide. The polypeptides of the vaccine composition may be fused to a HA-tag, Flag-tag, Myc-tag, V5-tag, Strep-tag, StrepII-tag, Sof-tag, His-Strep-Tag, Avi-tag, Calmodulin-tag, E-tag, S-tag, SBP-tag,TC-tag, VSV-tag, Xpress-tag, Ty-tag, Halo-tag, Nus-tag, Thioredoxin-tag, Fc-tag, chitin binding protein (CBP), maltose binding protein (MBP), glutathione-S-transferase (GST), green fluorescent protein (GFP). In a preferred embodiment the polypeptides of the vaccine composition are fused to a polyhistidine-tag, which may be composed of 6 or 12 His-residues, with 8 His-residues being preferred. A polypeptide tag is preferably fused to the polypeptides of the vaccine composition via a polypeptide linker. A preferred combination of polypeptide linker and 8 His-tag is shown in SEQ ID NO: 10.

A "polypeptide" refers to a molecule comprising a polymer of amino acids linked together by peptide bonds. Said term is not meant herein to refer to a specific length of the molecule and is therefore herein interchangeably used with the term "protein". When used herein, the term "polypeptide" or "protein" also includes a "polypeptide of interest" or "protein of interest" which is expressed by the expression cassettes or vectors or can be isolated from the host cells of the invention. A polypeptide comprises an amino acid sequence, and, thus, sometimes a polypeptide comprising an amino acid sequence is referred to herein as a "polypeptide comprising a polypeptide sequence". Thus, herein the term "polypeptide sequence" is interchangeably used with the term "amino acid sequence".

The term "amino acid" or "aa" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

An "epitope" is the part of an antigen that is recognized by the immune system, e.g. B cells or T cells. The term encompasses both conformational and linear (or sequential) epitopes. Conformational epitopes comprise discontinuous sections of the antigen's amino acid sequence, whereas linear epitopes are composed of a continuous section of the antigen's amino acid sequence. A conformational epitope may also comprise sections of two or more antigens' amino acid sequences. The term further includes cryptotopes and neotopes. "Cryptotopes" are epitopes which are hidden in the naturally occurring antigen, e.g. virus, but can become accessible when the antigen is not present in its natural conformation. "Neotopes" are epitopes found only in quaternary structures of proteins, but not in protein monomers.

B cell epitope is a region of an antigen (e.g., a native protein) recognized by either a particular membrane-bound B-cell receptor (BCR) or an antibody. A number of methods are readily available to identify or select B-cell epitopes, including x-ray crystallography, array-based oligopeptide scanning, site-directed mutagenesis, mutagenesis mapping, and phage display, as well as computational methods as reviewed by Sun et al. *Comput Math Methods Med.* 2013; 2013: 943636. For example, suitable methods include as structure-based prediction models, which rely on the 3D structure of antigen and epitope-related propensity scales, including geometric attributes and specific physicochemical properties. Structure-based algorithms and web servers (programs) include, e.g., EPSVR & EPMeta (http://sysbio.unl.edu/services/), EPCES (http://sysbio.unl.edu/services/EPCES/), and Epitopia (http://epitopia.tau.ac.il/). Mimotope-based prediction methods are combinatorial methods which require both antibody affinity-selected peptides and the 3D structure of antigen as input. Exemplary algorithms and programs based on mimotope-based prediction models include, e.g., MimoPro (http://informatics.nenu.edu.cn/MimoPro), PepSurf (http://pepitope.tau.ac.il and EpiSearch (http://curie.utmb.edu/episearch.html). Further, sequence-based prediction models are available which only rely on the primary sequence of an antigen, e.g. BEST and Zhang's method as reviewed in Sun et al. *Comput Math Methods Med.* 2013; 2013: 943636. In addition, binding sites prediction models can be used which infer methods that that focus on binding sites prediction of protein-protein interaction the interaction of an antigen and an antibody, e.g. ProMate, ConSurf, PINUP, and PIER.

T-cell epitopes are typically derived from processed protein antigens. A T cell epitope can be a CD4 T-cell epitope or a CD8 T-cell epitope. While cytotoxic (CD8) T-cells recognize intracellular peptides displayed by MHC class I molecules (CD8 T-cell epitopes), T helper cells recognize peptides that are taken up from the extracellular space and displayed by MHC class II molecules (CD4 T-cell epitopes). The peptide:MHC complex (pMHC) interacts with the T-cell receptor, leading to its activation and subsequent induction of a cellular immune response. A number of in silico methods for T cell epitope prediction and/or selection are available. For CD8+ T cell epitope prediction, NetCTL-1.2, EpiJen, or MAPPP can be used, as reviewed in Larsen et al. BMC Bioinformatics 2007, 8:424. For CD4+ T cells, computational models for epitope prediction have been reviewed by Oyarzún P et al. BMC Bioinformatics 2013, 14:52 and include data-driven methods which rely on peptide sequence comparisons to identify binding motifs, e.g. Rankpep, TEPITOPE, and NN-align, as well as structure-based methods which perform molecular modeling calculations in order to estimate the binding energies, thus offering independence from experimental binding data, e.g. NetMHCIIPan-2.0, TEPITOPEpan, and Predivac.

The term "Herpes Simplex Virus" and "HSV" are used interchangeably herein and refer generally to the viruses of the herpesviral Genus Simplexvirus, i.e. Ateline herpesvirus 1, Bovine herpesvirus 2, Cercopithecine herpesvirus 1, Cercopithecine herpesvirus 2, Cercopithecine herpesvirus 16, Human herpesvirus 1, Human herpesvirus 2, Macropodid herpesvirus 1, Macropodid herpesvirus 2, Saimiriine herpesvirus 1. Preferred viral species of the Genus Simplexvirus are viruses infecting humans. Even more preferred viral species are Herpes simplex virus 1 (HSV-1) and Herpes simplex virus 2 (HSV-2) which are also known as human herpesvirus 1 and 2 (HHV-1 and HHV-2), respectively.

The term "vaccine composition" as used herein relates to a composition comprising the multimeric complex of the present invention which can be used to prevent or treat a pathological condition associated with HSV in a subject. The "vaccine composition" may or may not include one or more additional components that enhance the immunological activity of the active component or such as buffers, reducing agents, stabilizing agents, chelating agents, bulking agents, osmotic balancing agents (tonicity agents); surfactants, polyols, anti-oxidants; lyoprotectants; anti-foaming agents; preservatives; and colorants, detergents, sodium salts, and/or antimicrobials etc. The vaccine composition may additionally comprise further components typical to pharmaceutical compositions. The vaccine of the present invention is, preferably, for human and/or veterinary use.

The vaccine composition may be sterile and/or pyrogen-free. The vaccine composition may be isotonic with respect to humans.

The vaccine composition preferably comprises a therapeutically effective amount of the multimeric complex of the invention or obtainable by the method of the invention.

The HSV polypeptide UL11 of the vaccine composition of the present invention preferably comprises an amino acid sequence which is 75% or more identical to the amino acid sequence of SEQ ID NO: 1, wherein said HSV polypeptide UL11 is capable of eliciting an immune response when administered in the form of a vaccine composition to a subject.

The term "UL11" when used herein relates to the tegument protein of HSV. SEQ ID NO: 1 depicts exemplarily an amino acid sequence of HSV-2 UL11, also deposited with NCBI GenBank under accession number AHG54674.1. However, the term "UL11" also encompasses UL11 polypeptides having an amino acid sequence which shares a certain degree of identity with the amino acid sequence shown in SEQ ID NO: 1 and also encompasses polypeptides having mutations relative to the reference sequence shown in SEQ ID NO: 1 as described herein. Accordingly, the term "UL11" encompasses polypeptides having an amino acid sequence identity of 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 74%, 73%, 72%, 71%, 70% or preferably 75% or more compared to the amino acid sequence of SEQ ID NO: 1 or polypeptides having up to 1, 2, 3, 4, 5, 6, 7, 8, 9, 10, 11, 12, 13, 14, 15, 16, 17, 18, 19, 20, 21, 22, 23, 25, 26, 27, 28, 29 or preferably 24 amino acid substitutions, insertions and/or deletions compared to the amino acid sequence of SEQ ID NO: 1. Preferred UL11 proteins can form a complex with UL16, UL21 and/or gE or the cytoplasmic tail of gE. Accordingly, preferred UL11 proteins can form a dimer with UL16 or gE or the cytoplasmic tail of gE, can form a trimer with UL16 and UL21 or with UL16 and gE or the cytoplasmic tail of gE and/or can form a tetramer with UL16, UL21 and gE or the cytoplasmic tail of gE.

"Sequence identity" or "% identity" refers to the percentage of residue matches between at least two polypeptide sequences aligned using a standardized algorithm. Such an algorithm may insert, in a standardized and reproducible way, gaps in the sequences being compared in order to optimize alignment between two sequences, and therefore achieve a more meaningful comparison of the two sequences. For purposes of the present invention, the sequence identity between two amino acid sequences is determined using the NCBI BLAST program version 2.3.0 (Jan. 13, 2016) (Altschul et al., Nucleic Acids Res. (1997) 25:3389-3402). Sequence identity of two amino acid sequences can be determined with blastp set at the following parameters: Matrix: BLOSUM62, Word Size: 3; Expect value: 10; Gap cost: Existence=11, Extension=1; Compositional adjustments: Conditional compositional score matrix adjustment.

The term "immune response" refers to the ability to induce a humoral and/or cell mediated immune response, preferably but not only in vivo. A humoral immune response comprises a B-cell mediated antibody response. A cell mediated immune comprises a T-cell mediated immune response, including but not limited to CD4+ T-cells and CD8+ T-cells. The ability of an antigen to elicit immune responses is called immunogenicity, which can be humoral and/or cell-mediated immune responses. An immune response of the present invention is preferably an immune response against HSV and even more preferably an immune response against a HSV infection in a subject.

The ability to induce a humoral and/or cell mediated immune response in vivo can be determined using a guinea pig model of genital HSV-2 infection, which accurately mirrors the disease in humans and represents a system to examine pathogenesis and therapeutic efficacy of candidate antiviral compounds and vaccines. It also serves as an ideal system to address the nature of both genital-resident and neural tissue-resident immune memory. Genital infection of guinea pigs results in a self-limiting vulvovaginitis with neurologic manifestations mirroring those found in human disease. Primary disease in female guinea pigs involves virus replication in genital epithelial cells which is generally limited to eight days. During this time, virus reaches sensory nerve endings and is transported by retrograde transport to cell bodies in the sensory ganglia and autonomic neurons in spinal cords. Following a brief period of acute replication at this site, the immune system usually resolves acute virus replication by day 15 post inoculation and the virus is maintained as a lifelong, latent infection of sensory neurons. Following recovering from primary HSV-2 genital infection guinea pigs experience episodic spontaneous recurrent infection and disease. HSV-2 recurrences may manifest as clinically apparent disease with erythematous and/or vesicular lesions on the perineum or as asymptomatic recurrences characterized by shedding of virus from the genital tract. Vaccine efficacy may for example be assessed using the guinea pig genital infection model. Animals may be infected intravaginally with $5\times10^1$ PFU, $5\times10^2$ PFU, $5\times10^3$ PFU, $5\times10^4$ PFU, $5\times10^6$ PFU, $5\times10^7$ PFU, $5\times10^8$ PFU, or $5\times10^9$ PFU and preferably $5\times10^5$ PFU of HSV-2 (e.g. strain MS). Animals may be immunized prior or post infection one, two, three, four, five or more times. Preferably, at day 15 post infection animals were immunized twice with 15 days interval. In general, any suitable route of administration may be used for immunization. However, animals are preferably immunized intramuscularly. Possible control groups are either mock-immunized with adjuvant-only (e.g. CpG 100 μg/Alum 150 μg) or with PBS (both negative controls), or with the HSV-2 dl5-29 mutant virus strain (positive control). Groups that are immunized with vaccine candidates combined with the adjuvant may receive a dose of 0.1 μg, 0.5 μg, 1 μg, 2 μg, 3 μg, 4 μg, 5 μg, 10 μg, 15 μg, 25 μg, 30 μg, 35 μg, 40 μg, 50 μg, 60 μg, 70 μg, 80 μg, 90 μg, 100 μg, 150 μg, 200 μg and preferably 20 μg of the respective antigen in each immunization round. As a read out vaginal swabs can be collected for evaluation of the frequency and magnitude of recurrent virus shedding, e.g. from day 0 post infection to day 200, day 1 post infection to day 180, day 3 post infection to day 160, day 5 post infection to day 140, day 7 post infection to day 120, day 10 post infection to day 100, day 12 post infection to day 90. Vaginal swabs can be collected every 1, 2, 3, 4, 5, 6, 7, 8, 9, or 10 days. Preferably, vaginal swabs are collected every day, from day 15 post infection to day 85. In the same time interval the severity (scores 0 to 4) and duration of recurrent genital herpetic lesions are scored daily. Preferably, at the end of study the antibody responses as well as the CD4+ and CD8+ T-cell responses are determined.

A variety of routes are applicable for administration of the vaccine composition of the present invention, including, but not limited to, orally, topically, transdermally, subcutaneously, intravenously, intraperitoneally, intramuscularly or intraocularly. However, any other route may readily be chosen by the person skilled in the art if desired.

The exact dose of the vaccine composition of the invention which is administered to a subject may depend on the purpose of the treatment (e.g. treatment of acute disease vs. prophylactic vaccination), route of administration, age, body weight, general health, sex, diet, time of administration, drug interaction and the severity of the condition, and will be ascertainable with routine experimentation by those skilled in the art. The administered dose is preferably an effective dose, i.e. effective to elicit an immune response.

The vaccine composition of the present invention may be administered to the subject one or more times, such as 2, 3, 4, 5, 6, 7, 8, 9, 10, or more times.

The "subject" as used herein relates to an animal, preferably a mammal, which can be, for instance, a mouse, rat, guinea pig, hamster, rabbit, dog, cat, or primate. Preferably, the subject is a human. However, the term "subject" also comprises cells, preferably mammalian cells, even more preferred human cells. Such a cell may be an immune cell, preferably a lymphocyte.

The HSV polypeptide UL16 of the vaccine composition the present invention preferably comprises an amino acid sequence which is 75% or more identical to the amino acid sequence of SEQ ID NO: 2, wherein said HSV polypeptide UL16 is capable of eliciting an immune response when administered in the form of a vaccine composition to a subject.

The term "UL16" when used herein relates to the tegument protein of HSV. SEQ ID NO: 2 depicts exemplarily an amino acid sequence of HSV-2 UL16, also deposited with NCBI GenBank under accession number AHG54679.1. However the term "UL16" also encompasses UL16 polypeptides having an amino acid sequence which shares a certain degree of identity with the amino acid sequence shown in SEQ ID NO: 2 and also encompasses polypeptides having mutations relative to the reference sequence shown in SEQ ID NO: 2 as described herein. Accordingly, the term "UL16" encompasses polypeptides having an amino acid sequence identity of 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 71%, 70%, 69%, 68%, 67% or preferably 72% or more compared to the amino acid sequence of SEQ ID NO: 2 or polypeptides having up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 105, 106, 107, 108, 109, 110, 111, 112, 113, 114, 115, 116, 117, 118, 119, 120, 121, 122, 123, or preferably 104 amino acid substitutions, insertions and/or deletions compared to the amino acid sequence of SEQ ID NO: 2. Preferred UL16 proteins can form a complex with UL11, UL21 and/or gE or the cytoplasmic tail of gE. Accordingly, preferred UL16 proteins can for a dimer with UL21 or UL11, can form a trimer with UL11 and UL21 and/or can form a tetramer with UL11, UL21 and gE or the cytoplasmic tail of gE.

The HSV polypeptide UL21 of the vaccine composition the present invention preferably comprises an amino acid sequence which is 80% or more identical to the amino acid sequence of SEQ ID NO: 3, wherein said HSV polypeptide UL21 is capable of eliciting an immune response when administered in the form of a vaccine composition to a subject.

The term "UL21" when used herein relates to the tegument protein of HSV. SEQ ID NO: 3 depicts exemplarily an amino acid sequence of HSV-2 UL21, also deposited with NCBI GenBank under accession number AHG54684.1. However the term "UL21" also encompasses UL21 polypeptides having an amino acid sequence which shares a certain degree of identity with the amino acid sequence shown in SEQ ID NO: 3 and also encompasses polypeptides having mutations relative to the reference sequence shown in SEQ ID NO: 3 as described herein. Accordingly, the term "UL21" encompasses polypeptides having an amino acid sequence identity of 99%, 98%, 97%, 96%, 95%, 94%, 93%, 92%, 91%, 90%, 89%, 88%, 87%, 86%, 85%, 84%, 83%, 82%, 81%, 79%, 78%, 77%, 76%, 75% or preferably 80% or more compared to the amino acid sequence of SEQ ID NO: 3 or polypeptides having up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, or preferably 134 amino acid substitutions, insertions and/or deletions compared to the amino acid sequence of SEQ ID NO: 3. Preferred UL21 proteins can form a complex with UL11, UL16 and/or gE or the cytoplasmic tail of gE. Accordingly, preferred UL21 proteins can for a dimer with UL16, can form a trimer with UL11 and UL16 and/or can form a tetramer with UL11, UL16 and gE or the cytoplasmic tail of gE.

As mentioned herein, the multimeric complex comprised in the vaccine composition of the present invention may also be a polypeptide complex comprising four polypeptides (i.e. a tetramer). Accordingly, the multimeric complex of the present invention comprising HSV polypeptides UL11, UL16, UL21 may further comprise HSV polypeptide gE. In this case the multimeric complex of the present invention comprises HSV polypeptides UL11, UL16, UL21, and gE.

The HSV polypeptide gE of the vaccine composition the present invention preferably comprises an amino acid sequence which is 70% or more identical to the amino acid sequence of SEQ ID NO: 4, wherein said HSV polypeptide gE is capable of eliciting an immune response when administered in the form of a vaccine composition to a subject.

The term "gE" when used herein may sometimes be referred to as "glycoprotein E". SEQ ID NO: 4 depicts exemplarily an amino acid sequence of HSV-2 gE, also deposited with NCBI GenBank under accession number AHG54732.1. However the term "gE" also encompasses gE polypeptides having an amino acid sequence which shares a certain degree of identity with the amino acid sequence shown in SEQ ID NO: 4 and also encompasses polypeptides having mutations relative to the reference sequence shown in SEQ ID NO: 4 as described herein. Accordingly, the term "gE" encompasses polypeptides having an amino acid sequence identity of 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 69%, 68%, 67%, 66%, 65% or preferably 70% or more compared to the amino acid sequence of SEQ ID NO: 4 or polypeptides having up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180 or preferably 165 amino acid substitutions, insertions and/or deletions compared to the amino acid sequence of SEQ ID NO: 4. Preferred gE proteins can form a complex with UL11, UL16 and UL21. Accordingly, preferred gE proteins can form a dimer with UL11, a trimer with UL11 and UL16 and a tetramer with UL11, UL16 and UL21.

In a further preferred embodiment of the present invention the multimeric complex comprising HSV polypeptides UL11, UL16, UL21 comprised in the vaccine composition of the present invention may also be a tetramer comprising the cytoplasmic domain of HSV polypeptide gE. In this case the multimeric complex of the present invention comprises HSV polypeptides UL11, UL16, UL21, and the cytoplasmic domain of gE.

The cytoplasmic domain of gE of the vaccine composition of the present invention preferably comprises an amino acid sequence as set forth in SEQ ID NO: 5. However, it is also envisioned herein that the cytoplasmic domain of gE comprises an amino acid sequence having a sequence identity of 99%, 98%, 97%, 96%, 95%, 94%, 93%, 92%, 91%, 90%, 89%, 88%, 87%, 86%, 85%, 84%, 83%, 82%, 81%, 79%, 78%, 77%, 76%, 75% or preferably 80% or more compared to the amino acid sequence of SEQ ID NO: 5 or polypeptides having up to 1, 2, 3, 4, 5, 6, 7, 8, 9, 10, 11, 12, 13, 14, 15, 16, 17, 18, 19, 20, 21, 22, 24, 25, 26, 27, or preferably 23 amino acid substitutions, insertions and/or deletions compared to the amino acid sequence of SEQ ID NO: 5. Preferred cytoplasmic domains of gE can form a complex with UL11, UL16 and UL21. Accordingly, preferred cytoplasmic domains of gE can form a dimer with UL11, a trimer with UL11 and UL16 and a tetramer with UL11, UL16 and UL21.

The HSV polypeptide UL48 of the vaccine composition of the present invention preferably comprises an amino acid sequence which is 80% or more identical to the amino acid sequence of SEQ ID NO: 6, wherein said HSV polypeptide UL48 is capable of eliciting an immune response when administered in the form of a vaccine composition to a subject.

The term "UL48" when used herein relates to the tegument protein VP16 of HSV. SEQ ID NO: 6 depicts exemplarily an amino acid sequence of HSV-2 UL48, also deposited with NCBI GenBank under accession number AHG54712.1. However, the term "UL48" also encompasses UL48 polypeptides having an amino acid sequence which shares a certain degree of identity with the amino acid sequence shown in SEQ ID NO: 6 and also encompasses polypeptides having mutations relative to the reference sequence shown in SEQ ID NO: 6 as described herein. Accordingly, the term "UL48" encompasses polypeptides having an amino acid sequence identity of 99%, 98%, 97%, 96%, 95%, 94%, 93%, 92%, 91%, 90%, 89%, 88%, 87%, 86%, 85%, 84%, 83%, 82%, 81%, 79%, 78%, 77%, 76%, 75%, or preferably 80% or more compared to the amino acid sequence of SEQ ID NO: 6 or polypeptides having up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 99, 100, 101, 102, 103, 104, 105, 106, 107, 108, 109, 110, 111, 112, 113, 114, 115, 116, 117, 118, 119, 120, 121, 122, 123 or preferably 98 amino acid substitutions, insertions and/or deletions compared to the amino acid sequence of SEQ ID NO: 6. Preferred UL48 proteins can form a dimer with UL49 or can form a trimer with UL49 and gE or the cytoplasmic tail of gE.

The HSV polypeptide UL49 of the vaccine composition the present invention preferably comprises an amino acid sequence which is 62% or more identical to the amino acid sequence of SEQ ID NO: 7, wherein said HSV polypeptide UL49 is capable of eliciting an immune response when administered in the form of a vaccine composition to a subject.

The term "UL49" when used herein relates to the tegument protein VP22 of HSV. SEQ ID NO: 7 depicts exemplarily an amino acid sequence of HSV-2 UL49, also deposited with NCBI GenBank under accession number AKC42813.1. However the term "UL49" also encompasses UL49 polypeptides having an amino acid sequence which shares a certain degree of identity with the amino acid sequence shown in SEQ ID NO: 7 and also encompasses polypeptides having mutations relative to the reference sequence shown in SEQ ID NO: 7 as described herein. Accordingly, the term "UL49" encompasses polypeptides having an amino acid sequence identity of 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 74%, 73%, 72%, 71%, 69%, 68%, 67%, 66%, 65%, 64%, 63%, 61%, 60%, 59%, 58%, 57% or preferably 62% or more compared to the amino acid sequence of SEQ ID NO: 2 or polypeptides having up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 116, 117, 118, 119, 120, 121, 122, 123, 124, 125, 126, 127, 128, 129, 130 or preferably 115 amino acid substitutions, insertions and/or deletions compared to the amino acid sequence of SEQ ID NO: 7. Preferred UL49 proteins can form a complex with UL48 and/or gE or the cytoplasmic tail of gE. Accordingly, preferred UL49 proteins can form a dimer with UL48 or gE or the cytoplasmic tail of gE or can form a trimer with UL48 and gE or the cytoplasmic tail of gE.

In a further preferred embodiment of the present invention the multimeric complex comprising HSV polypeptides UL48, UL49 comprised in the vaccine composition of the present invention may also be a trimer comprising the cytoplasmic domain of HSV polypeptide gE. In this case the multimeric complex of the present invention comprises HSV polypeptides UL48, UL49 and the cytoplasmic domain of gE.

The HSV polypeptide UL31 of the vaccine composition of the present invention preferably comprises an amino acid sequence which is 85% or more identical to the amino acid sequence of SEQ ID NO: 8, wherein said HSV polypeptide UL31 is capable of eliciting an immune response when administered in the form of a vaccine composition to a subject.

The term "UL31" when used herein relates to the virion egress protein of HSV. SEQ ID NO: 8 depicts exemplarily an amino acid sequence of HSV-2 UL31, also deposited with NCBI GenBank under accession number AHG54695.1. However, the term "UL31" also encompasses UL31 polypeptides having an amino acid sequence which shares a certain degree of identity with the amino acid sequence shown in SEQ ID NO: 8 and also encompasses polypeptides having mutations relative to the reference sequence shown in SEQ ID NO: 8 as described herein. Accordingly, the term "UL31" encompasses polypeptides having an amino acid sequence identity of 99%, 98%, 97%, 96%, 95%, 94%, 93%, 92%, 91%, 90%, 89%, 88%, 87%, 86%, 84%, 83%, 82%, 81%, 80%, or preferably 85% or more compared to the amino acid sequence of SEQ ID NO: 1 or polypeptides having up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61 or preferably 46 amino acid substitutions, insertions and/or deletions compared to the amino acid sequence of SEQ ID NO: 8. Preferred UL31 proteins can form a dimer with UL34.

The HSV polypeptide UL34 of the vaccine composition the present invention preferably comprises an amino acid sequence which is 70% or more identical to the amino acid sequence of SEQ ID NO: 9, wherein said HSV polypeptide UL34 is capable of eliciting an immune response when administered in the form of a vaccine composition to a subject.

The term "UL34" when used herein relates to the virion egress protein of HSV. SEQ ID NO: 9 depicts exemplarily an amino acid sequence of HSV-2 UL34, also deposited with NCBI GenBank under accession number AHG54698.1. However the term "UL34" also encompasses UL34 polypeptides having an amino acid sequence which shares a certain degree of identity with the amino acid sequence shown in SEQ ID NO: 9 and also encompasses polypeptides having mutations relative to the reference sequence shown in SEQ ID NO: 9 as described herein. Accordingly, the term "UL34" encompasses polypeptides having an amino acid sequence identity of 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75% 74%, 73%, 72%, 71%, 69%, 68%, 67%, 66%, 65% or preferably 70% or more compared to the amino acid sequence of SEQ ID NO: 2 or polypeptides having up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 76, 77, 78, 79, 80, 81, 82, 83, 84, 85, 86, 87, 88, or preferably 75 amino acid substitutions, insertions and/or deletions compared to the amino acid sequence of SEQ ID NO: 9. Preferred UL34 proteins can for a dimer with UL31.

As stated, each protein of the invention, may contain mutations, such as insertions, deletions and substitutions relative to the reference sequences shown in SEQ ID NO: 1 (UL11), SEQ ID NO: 2 (UL16), SEQ ID NO: 3 (UL21), SEQ ID NO: 4 (gE), SEQ ID NO: 5 (cytoplasmic domain of gE), SEQ ID NO: 6 (UL48), SEQ ID NO: 7 (UL49), SEQ ID NO: 8 (UL31) and SEQ ID NO: 9 (UL34), as long as these mutations are not detrimental to the use of the proteins as antigens in the vaccine composition of the present invention. In addition, such mutations should not prevent the capacity of the proteins to form a multimeric complex of the invention. The formation of a multimeric complex of the invention can be tested by performing protein purification, and analyzing the proteins by e.g. non-reducing PAGE, Western blot and/or size exclusion chromatography. In particular, each protein may comprise a tag which, e.g., may facilitate detection, purification and/or enhances solubility.

In a further preferred embodiment of the present invention the polypeptides of the multimeric complex of the vaccine composition of the present invention are HSV-1 polypeptides.

In a further preferred embodiment of the present invention the polypeptides of the multimeric complex of the vaccine composition of the present invention are HSV-2 polypeptides.

The vaccine composition of the invention may further comprise a pharmaceutically acceptable carrier or adjuvant.

The terms "carrier" and "excipient" are used interchangeably herein. Pharmaceutically acceptable carriers include, but are not limited to diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal $SiO_2$), solvents/co-solvents (e.g. aqueous vehicle, Propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), anti-foaming agents (e.g. Simethicone), thickening agents (e.g. methylcellulose or hydroxyethylcellulose), sweetening agents (e.g. sorbitol, saccharin, aspartame, acesulfame), flavouring agents (e.g. peppermint, lemon oils, butterscotch, etc), humectants (e.g. propylene, glycol, glycerol, sorbitol). Further pharmaceutically acceptable carriers are (biodegradable) liposomes; microspheres made of the biodegradable polymer poly(D, L)-lactic-coglycolic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable excipients are inter alia described in Remington's Pharmaceutical Sciences, 15th Ed., Mack Publishing Co., New Jersey (1991) and Bauer et al., Pharmazeutische Technologie, 5th Ed., Govi-Verlag Frankfurt (1997). The person skilled in the art will readily be able to choose suitable pharmaceutically acceptable carriers, depending, e.g., on the formulation and administration route of the pharmaceutical composition.

The term "adjuvant" as used herein refers to a substance that enhances, augments or potentiates the host's immune response (antibody and/or cell-mediated) to an antigen or fragment thereof. Exemplary adjuvants for use in accordance with the present invention include inorganic compounds such as alum, aluminum hydroxide, aluminum phosphate, calcium phosphate hydroxide, the TLR9 agonist CpG oligodeoxynucleotide, the TLR4 agonist monophosphoryl lipid (MPL), the TLR4 agonist glucopyranosyl lipid (GLA), the water in oil emulsions Montanide ISA 51 and 720, mineral oils, such as paraffin oil, virosomes, bacterial products, such as killed bacteria *Bordetella pertussis, Mycobacterium bovis*, toxoids, nonbacterial organics, such as squalene, thimerosal, detergents (Quil A), cytokines, such as IL-1, IL-2, IL-10 and IL-12, and complex compositions such as Freund's complete adjuvant, and Freund's incomplete adjuvant. Generally, the adjuvant used in accordance with the present invention preferably potentiates the immune response to the multimeric complex of the invention and/or modulates it towards the desired immune responses.

The term "pharmaceutically acceptable" means a non-toxic material that does not interfere with the effectiveness of the biological activity of the multimeric complex according to the present invention.

Purification

"Purifying" in all its grammatical forms means removing undesirable compounds, e.g. cells, cell debris, culture medium, baculovirus, either intact or non-intact baculoviruses, etc. Suitable purification methods depending on the expression system, yield, etc. are readily available in the prior art. E.g., purification may include ion exchange chromatography, hydrophobic interaction chromatography, size exclusion chromatography, affinity chromatography and/or mixed-mode chromatography all of which have been described extensively before. As said, the purification step includes, inter alia, removing baculoviruses. Such baculoviruses may be contained in the culture medium and/or supernatant obtainable from host cells which were infected with a baculoviral vector or BacMam vector. It is preferred that such baculoviruses be removed when purifying a multimeric complex of the present invention.

Purifying as used herein also includes that host cells which co-express HSV proteins may be removed from the culture medium. Said culture medium comprises preferably a multimeric complex of the present invention, since said host cells may secrete said multimeric complex. Removing host cells from culture medium may be done by mechanical force, such as by centrifugation or by filtration. Filtration is preferably done by using filtration medium, such as microfiltration filters or on depth-filters. Microfiltration filters may be composed of polyethersulfone or regenerated cellulose. On depth-filters may be composed of polypropylene or glass fibers.

However, it is also envisaged that said host cell do not necessarily have to secrete said multimeric complex. If so, then said host cells may be harvested. After harvest, said host cells may be broken up, e.g., enzymatically or mechanically in order to release a multimeric complex which may then be purified as described herein.

After purification, it is envisaged that a chelating agent is added to the multimeric complex.

Storage

"Storing" in all its grammatical forms means preserving (for future use), preferably under conditions which maintain the multimeric complex of the invention in its intact or functional form, i.e. the multimeric complex preferably resembles its naturally occurring form. It is thus envisaged that storing conditions do not promote (or do even prevent) disintegration of the multimeric complex of the invention. The term "disintegration" is to be understood in its broadest sense herein and can mean "disassembly" and/or "denaturation". Storage of the multimeric complex of the invention is envisaged in a buffer solution comprising a chelating agent and/or a stabilizing agent.

In general, any chelating agent and/or stabilizing agent is suitable as long as it enables storage of the multimeric complex of the invention and does not promote its disintegration.

The buffer solution in accordance with the present invention may comprise Tris buffer, NaCl, KCl, PBS, HEPES buffer.

Use of the Vaccine Composition

The present invention also pertains to the use of the vaccine composition in a method of inducing an immune response against HSV in a subject.

In a preferred embodiment of the present invention the vaccine composition is used for the treatment, prevention or amelioration of HSV infection or preventing reactivation of HSV.

Accordingly, the vaccine composition may be used in fighting diseases caused by HSV and/or related symptoms. It is also envisaged that the vaccine composition of the present invention may be used for clearing the virus in a subject, i.e. after treatment no HSV can be detected in a suitable sample obtained from the subject using suitable methods known to those of ordinary skill in the art, e.g. PCR, ELISA etc. Thus, the vaccine composition of the present invention may be used to block primary infection, stop primary disease, block virus reactivation and re-infection, and to block latency.

To reduce the chance of genital herpes a prophylactic vaccine to prevent the first HSV infection of the mother is desirable, whereas an effective therapy is needed in the case a mother is diagnosed with an active HSV infection. A multimeric complex of the present invention may be applied as a prophylactic vaccine, e.g. for expectant mothers or children, or as a therapeutic vaccine in seropositive women to prevent subclinical reactivation at the time of delivery.

In a further preferred embodiment of the present invention the vaccine composition is used in a method for inducing an immune response against HSV-1 or HSV-2 in a subject.

Vector

The present invention further pertains to a vector comprising a polynucleotide encoding UL11, UL16 and UL21, and optionally gE or the cytoplasmic domain of gE. In a further embodiment of the present invention the vector may also comprise a polynucleotide encoding UL11 and UL16. In a further embodiment of the present invention the vector may also comprise a polynucleotide encoding UL16 and UL21. The present invention further pertains to a vector comprising a polynucleotide encoding UL48, UL49 and gE or the cytoplasmic domain of gE. In a further embodiment of the present invention the vector may also comprise a polynucleotide encoding UL48 and UL49. In a further embodiment of the present invention the vector may also comprise a polynucleotide encoding UL49 and gE or the cytoplasmic domain of gE. The present invention further pertains to a vector comprising a polynucleotide encoding UL31 and UL34. Generally, the genes encoding the HSV proteins of the complex of the invention can also be present on more than one vector, e.g. on two vectors. Accordingly, one, two, or three of the genes are on a first vector, while the remaining gene/s are on a second vector. However, each of the genes may also be on a separate vector. Preferably, however, said genes are present on a single vector. Genes may also be present in polygenic form (EP1945773).

The term "vector" as used herein refers to a nucleic acid sequence into which an expression cassette comprising a gene encoding the protein of interest may be inserted or cloned. Furthermore, the vector may encode an antibiotic resistance gene conferring selection of the host cell. Preferably, the vector is an expression vector.

The vector can contain elements for propagation in bacteria (e.g. E. coli), yeast (e.g. S. cerevisiae), insect cells and/or mammalian cells. Preferably, said vector is a Baculovirus vector or a Baculovirus BacMam vector. The vector may have a linear, circular, or supercoiled configuration and may be complexed with other vectors or other material for certain purposes. The vector may also be integrated in the host cell genome.

In the BacMam system, baculovirus vectors are used to deliver genes into mammalian cells. The BacMam system can be used for gene delivery to a broad range of cell lines and primary cells as host cells, an exemplary list of which is included elsewhere herein. The unmodified baculovirus is able to enter mammalian cells, however its genes are not expressed unless a mammalian recognizable promoter is incorporated upstream of a gene of interest. Thus, it is envisaged that the BacMam vector of the invention comprises a mammalian promoter upstream the genes encoding the proteins of the multimeric complex of the invention. The vector may comprise additional elements as described elsewhere herein, e.g. antibiotic resistance genes, elements for propagation in E. coli, S. cerevisiae etc.

The vector may contain one or more further elements, including, e.g., an origin of replication, promoters, cloning sites, genetic markers, antibiotic resistance genes, epitopes, reporter genes, targeting sequences and/or protein purification tags. The person skilled in the art will readily know which elements are appropriate for a specific expression system.

In particular, the vector in accordance with the invention may further contain elements for propagation in bacteria (E. coli), yeast (S. cerevisiae), insect cells and/or mammalian cells, such as origin of replication, selection markers, etc.

It is envisaged that the vector comprises a promoter for gene expression. Each of the gene encoding the proteins of the invention described herein is driven by a promoter. The promoters are preferably selected from the group consisting of polh, p10 and $p_{XIV}$ very late baculoviral promoters, vp39 baculoviral late promoter, vp39polh baculoviral late/very late hybrid promoter, pca/polh, pcna, etl, p35, egt, da26 baculoviral early promoters; CMV-IE1, UBc. EF-1, RSVLTR, MT, Simian virus 40 promoter, CAG promoter (beta-actin promoter with CMV-IE1 enhancer), hepatitis B virus promoter/enhancer, human ubiquitin C promoter, hybrid neuronal promoter, $p_{DS47}$, Ac5, and $P_{GAL}$ and $P_{ADH}$. Each of the genes is followed by a terminator sequence such as HSVtk terminator, SV40 terminator, or bovine growth hormone (BGH) terminator.

The terms "polynucleotide", "nucleotide sequence" or "nucleic acid molecule" are used interchangeably herein and refer to a polymeric form of nucleotides which are usually linked from one deoxyribose or ribose to another. The term "polynucleotide" preferably includes single and double stranded forms of DNA or RNA. A nucleic acid molecule of this invention may include both sense and antisense strands of RNA (containing ribonucleotides), cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

In this regard, a nucleic acid being an expression product is preferably a RNA, whereas a nucleic acid to be introduced into a cell is preferably DNA or RNA, e.g. synthetic DNA, genomic DNA or cDNA.

Also envisaged is a vaccine composition comprising a nucleic acid or a vector encoding the multimeric complex as disclosed herein. Said nucleic acid or vector can be DNA- or RNA-based. Suitable vectors for use in accordance with the vaccine composition include DNA-based vectors such as baculovirus vectors, BacMam vectors, adenovirus vectors, lentiviral vectors, AAV vectors, herpesvirus vectors, poxvirus vectors, and Epstein-Barr virus (EBV) vectors. The use of naked DNA; e.g. in the form of a plasmid, and optionally complexed and/or in stabilized form (e.g. lipoplexes, polyplexes, dendrimers, virosomes and complexes with inorganic nanoparticles) is also envisaged. Suitable RNA-based vectors include retroviral vectors, Semliki forest virus (SFV), Sindbis virus (SIN) and Venezuelan equine encephalitis virus (VEE) vectors.

The vaccine composition comprising the multimeric complex and the vaccine composition comprising the nucleic acid or the vector encoding the multimeric complex may be used in a prime boost regimen. In the prime boost regimen, a prime/boost vaccine is used which is composed of two or more types of vaccine including a vaccine used in primary immunization (prime or priming) and a vaccine used in booster immunization (boost or boosting). The vaccine used in primary immunization and the vaccine used in booster immunization may differ from each other. Primary immunization and boosting immunization may be performed sequentially, this is, however, not mandatory. The prime/boost regimen includes, without limitation, e.g. DNA prime/protein boost. However, the boosting composition can also be used as priming composition and said priming composition is used as boosting composition.

Host Cell

The present invention further pertains to a host cell comprising a vector comprising a polynucleotide encoding UL11, UL16 and UL21, and optionally gE or the cytoplasmic domain of gE. In a further embodiment of the present invention the host cell may also comprise a vector comprising a polynucleotide encoding UL11 and UL16. In a further embodiment of the present invention the host cell may also comprise a vector comprising a polynucleotide encoding UL16 and UL21.

The present invention further pertains to a host cell comprising a vector comprising a polynucleotide encoding UL48, UL49 and gE or the cytoplasmic domain of gE. In a further embodiment of the present invention the host cell may also comprise a vector comprising a polynucleotide encoding UL48 and UL49. In a further embodiment of the present invention the host cell may also comprise a vector comprising a polynucleotide encoding UL49 and gE or the cytoplasmic domain of gE.

The present invention further pertains to a host cell comprising a vector comprising a polynucleotide encoding UL31 and UL34.

The host cell may be an insect cell or mammalian cell. The host cell may also be bacteria (e.g. E. coli) or yeast (e.g. S. cerevisiae). Generally, any host cell that is suitable to express nucleic acid molecules to produce the multimeric complex of the invention may be used. However, preferred are insect and mammalian host cells. Even more preferred are insect host cells. The host cell used in accordance with the invention may be an insect cell, such as Sf9, Sf21, Super Sf9-1 (VE-1), Super Sf9-2 (VE-2), Super Sf9-3 (VE-3), Hi-5, Express Sf+, and S2 Schneider cells, with Hi-5 being preferred [Oxford Expression Technologies, Cat. No. 600103, Oxford, UK; Fath-Goodin et al. (2006), Adv. Virus Res. 68, 75-90; Kroemer et al. (2006), J. Virol. 80(24), 12291-12228 and US20060134743.]. Exemplary mammalian host cells that may be used are known in the art and include immortalised cell lines available from the American Type Culture Collection (ATCC) including, but not limited to, HEK293, HEK293F, CHO, HeLa, HUVEC, HUAEC, Huh7, HepG2, BHK, MT-2, Cos-7, Cos-1, C127, 3T3, human foreskin fibroblasts (HFF), bone-marrow fibroblasts, Bowes melanoma, primary neural cells, or epithelial cells. In the BacMam system, baculovirus expression vectors are used to deliver genes to mammalian cells.

Method for Production

The present invention further provides a method for producing the vaccine composition comprising the multimeric complex, comprising (i) culturing a host cell of the present invention;
(ii) obtaining a multimeric complex;
(iii) and admixing said multimeric complex with a pharmaceutically acceptable carrier or adjuvant.

It is to be noted that the embodiments described in the context of the multimeric complex of the invention also apply to the method of the invention, mutatis mutandis.

The multimeric complex may be expressed in a host cell, preferably insect cell or mammalian cell, by using baculovirus, e.g., a Baculovirus expression system or BacMam expression system. An "expression vector" is defined herein as vehicle used to transfer genetic material to a target host cell where the genetic material can be expressed. An "expression system" is the combination of an expression vector, and the host cell for the vector that provide a context to allow foreign gene expression in the host cell. The complex of the present invention may be expressed transiently or stably. Accordingly, a host cell of the present invention can be transiently transfected with the expression vector or can be stably transfected with the expression vector, e.g. via integration of the vector in the host cell genome resulting in a stable cell line.

The baculovirus expression system is typically based on the introduction of a foreign gene into a nonessential viral genome region, e.g. via homologous recombination with a transfer vector containing a target gene. The resulting recombinant baculovirus may lack one of the nonessential genes (e.g. polh, v-cath, chiA) replaced with a foreign gene encoding the heterologous protein which can be expressed in a suitable host cell. These techniques are generally known to those skilled in the art and have been reviewed e.g. by Kosta et al. *Nat Biotechnol.* 2005; 23(5):567-75. A specific approach for preparing recombinant baculovirus vectors is the Bac-to-Bac® baculovirus system (Invitrogen).

The recombinant baculovirus expression vector may be capable of replication in a host cell and optionally in a prokaryotic cell such as *E. coli*. According to the present invention, any baculovirus expression vector derived from a baculovirus commonly used for the recombinant expression of proteins may be used. For example, the baculovirus vector may be derived from, e.g., AcMNPV, *Bombyx mori* (Bm)NPV, *Helicoverpa armigera* (Hear) NPV) or *Spodoptera exigua* (Se) MNPV. The baculovirus vector may be a bacmid.

It must be noted that as used herein, the singular forms "a", "an", and "the", include plural references unless the context clearly indicates otherwise. Thus, for example, reference to "an expression cassette" includes one or more of the expression cassettes disclosed herein and reference to "the method" includes reference to equivalent steps and methods known to those of ordinary skill in the art that could be modified or substituted for the methods described herein.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

The term "about" or "approximately" as used herein means within 20%, preferably within 10%, and more preferably within 5% of a given value or range. It includes also the concrete number, e.g., about 20 includes 20.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well-known in the art. Generally, nomenclatures used in connection with techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e. g., Sambrook et al., Molecular Cloning: A Laboratory Manual, 3rd ed., Cold Spring Harbor Laboratory Press, Cold Spring Harbor, N.Y. (2001); Ausubel et al., Current Protocols in Molecular Biology, J, Greene Publishing Associates (1992, and Supplements to 2002); Handbook of Biochemistry: Section A Proteins, Vol I 1976 CRC Press; Handbook of Biochemistry: Section A Proteins, Vol II 1976 CRC Press. The nomenclatures used in connection with, and the laboratory procedures and techniques of, molecular and cellular biology, protein biochemistry, enzymology and medicinal and pharmaceutical chemistry described herein are those well-known and commonly used in the art.

DESCRIPTION OF THE FIGURES

FIG. 1: Amino acid sequences of HSV proteins of the present invention

FIG. 2: Example of a SDS-PAGE and a western blot showing the UL21/UL16/UL11-His trimer FIG. 5: Example of a SDS-PAGE and a western blot showing the UL31-His/UL34 dimer FIG. 6: Example of a SDS-PAGE and a western blot showing the UL31/UL34-His dimer FIG. 7: Example of a SDS-PAGE and a western blot showing the UL31/UL34-His dimer

EXAMPLES

The following Examples illustrate the invention, but are not to be construed as limiting the scope of the invention.

Example 1

The UL21/UL16/UL11-His trimer was expressed in Hi-5 insect cells and released from cell pellets after proper lysis. The trimer was subsequently purified using IMAC and a 0-500 mM imidazole buffer system (50 mM Hepes, 500 mM NaCl, pH 7.0, 1 mM TCEP, 10% glycerol). Impurities were washed out by applying 25 mM imidazole to the column. The trimer was then eluted with 250 mM imidazole, followed by dialysis in Hepes buffer without imidazole (50 mM Hepes, 150 mM NaCl, pH 7.0, 0.5 mM TCEP, 10% glycerol). FIG. 2 (A) An example of a SDS-PAGE is shown. The UL11-His is represented by a faint band on this blot which is, however, revealed using an anti-His antibody. FIG. 2 (B) An example of the western blot performed using an anti-His antibody to detect UL11-His is shown. Labeling in both examples: 1. Standards, 2. Filtrated supernatant, 3. Cell pellet, 4. Flowthrough, 5-10. Fractions A5, B9, B11, C3, C6, E6, 11. Pool of fractions B9-C3, 12. Pellet after dialysis, 13. Supernatant after dialysis, 14. Filtrated protein.

Example 2

Figure 3:
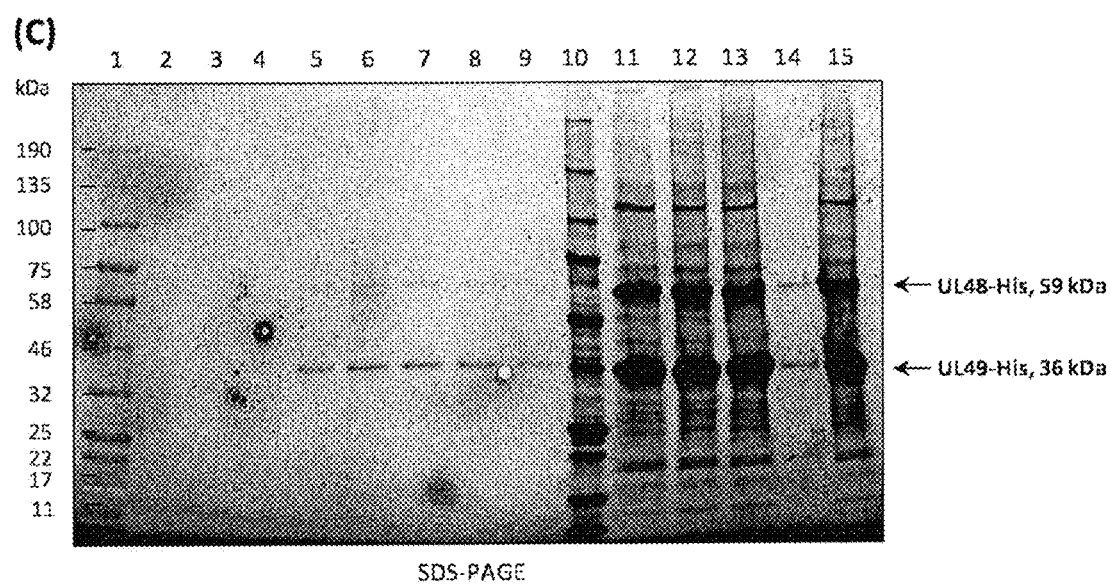
FIG. 3: Examples of SDS-PAGEs showing the UL48-His/UL49-His dimer

The UL48-His/UL49-His dimer was expressed in Hi-5 insect cells and released from cell pellets after proper lysis. The dimer was subsequently purified using IMAC and a 0-500 mM imidazole buffer system (TBS buffer, 500 mM NaCl, pH 7.4). Impurities were washed out by applying 50 mM imidazole to the column. The dimer was then eluted with 350 mM imidazole, followed by dialysis in TBS buffer without imidazole (TBS buffer, 500 mM NaCl, pH 7.4, 10% glycerol). The product was further subjected to Size Exclusion Chromatography (SEC) to prove the existence of the dimer. A peak corresponding to the expected size of the UL48-His/UL49-His dimer was present. FIG. 3 (A) shows an example of an SDS-PAGE before SEC is shown. Labeling: 1. Standards-a, 2. Supernatant, 3. Debris pellet, 4. Filtrated supernatant, 5. Wash of unbound fraction, 6-14. Fractions 2A9, 2A12, 2C4, 2C10, 2C12, 2C12 filtrated, 2D2, 2D6, 2D7. FIGS. 3 (B) and (C) show an example of an SDS-PAGE after SEC and aceton precipitation of the samples. In panel (C) the same gel is shown as in (B), however overexposed to better visualize the low intensity bands. Labeling: 1. Standards-b, 2-9. Fractions SEC aceton precipitated A8, A12, B1, B2, B3, B4, B5, B6. 10. Standards-a, 11. Pool IMAC of fractions 2C11, 2D1 and 2D2, 12. Pool IMAC dialysate, 13. Pool IMAC supernatant of dialysate, 14. Pool IMAC pellet, 15. Pool IMAC filtrated protein.

Example 3

Figure 4:
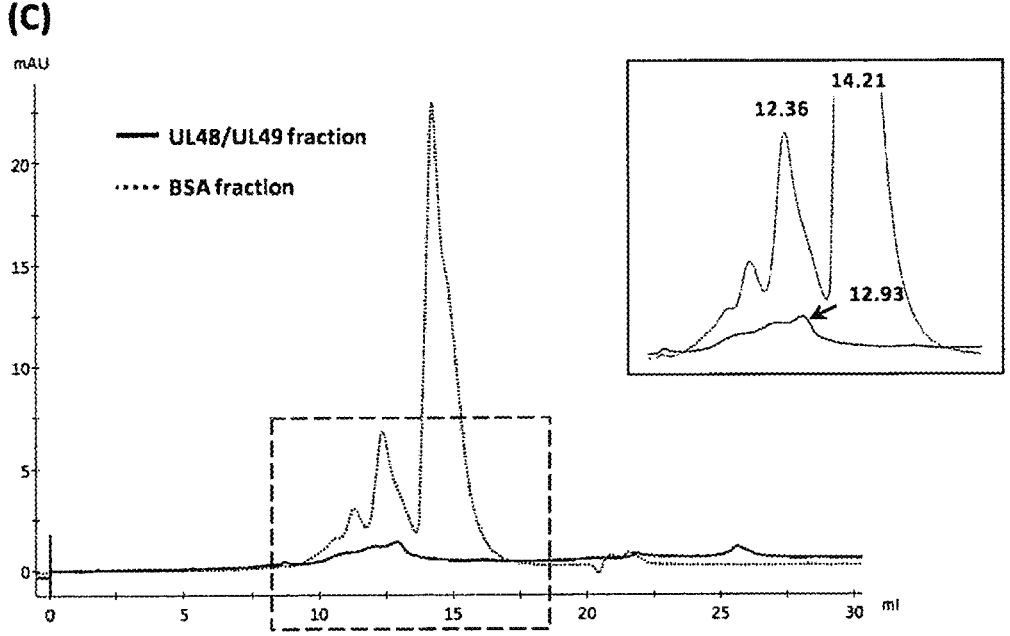
FIG. 4: Example of a Size Exclusion Chromatography showing the UL48-His/UL49-His dimer

Size Exclusion Chromatography (SEC) was carried out for the analysis of the UL48-His/UL49-His product in TBS buffer, 500 mM NaCl, pH 7.4. Runs were performed using a Superdex 200 Increase 10/300 GL SEC column and a flow rate of 0.5 mL/min. The column was calibrated using 3 mg/mL BSA as a standard. In FIG. 4 (A) the peaks at 12.36 and 14.21 mL retention volumes correspond to the dimer and monomer (66 kDa) of the BSA calibration standard, respectively. In FIG. 4 (B) the main peak at 12.93 mL represents the UL48/UL49 dimer, whereas the peak at 12.16 mL likely corresponds to a tetramer formation of the UL48 and UL49 subunits. FIG. 4 (C) shows an overlay of the two independent runs shown in (A) and (B). The inlet shows a zoom-in of the area between 8.5 and 18 mL retention volumes.

Example 4

The UL31-His/UL34 dimer was expressed in Hi-5 insect cells and released from cell pellets after proper lysis. The dimer was subsequently purified using IMAC and a 0-500 mM imidazole continuous gradient buffer system (50 mM Hepes, 500 mM NaCl, pH 7.0, 1 mM TCEP). FIG. 5 (A) An example of an SDS-PAGE is shown. One of the two most concentrated fractions is marked with an asterisk. FIG. 5 (B) An example of the western blot performed using an anti-His antibody to detect UL31-His is shown. Labeling in both examples: 1. Standards, 2. Supernatant, 3. Filtrated supernatant, 4. Cell pellet, 5. Flowthrough, 6. Wash of unbound protein, 7-13. Fractions A8, A10, B4, B8, B11, C2, C7.

Example 5

The UL31/UL34-His dimer was expressed in Hi-5 insect cells and released from cell pellets after proper lysis. The dimer was subsequently purified using IMAC and a 25-500 mM imidazole continuous gradient buffer system (50 mM Hepes, 500 mM NaCl, pH 7.0, 1 mM TCEP). FIG. 6 (A) An example of an SDS-PAGE is shown. One of the two most concentrated fractions is marked with an asterisk. FIG. 6 (B) An example of the western blot performed using an anti-His antibody to detect UL34-His is shown. Labeling in both examples: 1. Standards, 2. Supernatant, 3. Filtrated supernatant, 4. Cell pellet, 5. Flowthrough, 6. Wash of unbound protein, 7-13. Fractions A8, A10, B4, B8, B11, C2, C7.

Example 6

The UL31/UL34-His dimer was expressed in Hi-5 insect cells and released from cell pellets after proper lysis. The dimer was subsequently purified using IMAC and a 0-500 mM imidazole buffer system (50 mM Hepes, 500 mM NaCl, pH 7.0, 1 mM TCEP, 10% glycerol). Impurities were washed out in two steps by applying 50 mM and 75 mM imidazole to the column. The dimer was then eluted with 350 mM imidazole, followed by dialysis in Hepes buffer without imidazole (50 mM Hepes, 500 mM NaCl, pH 7.0, 0.5 mM TCEP, 10% glycerol). FIG. 7 (A) An example of an SDS-PAGE is shown. FIG. 7 (B) An example of the western blot performed using an anti-His antibody to detect UL34-His is shown. Labeling in both examples: 1. Standards, 2. Culture cell pellet, 3. Lysate, 4. Supernatant, 5. Crude pellet, 6. Filtrated supernatant, 7. Flowthrough, 8-16. Fractions B12, C2, C5, C7, C11 and F1 17. Pool of fractions C3-C7, 18. Dialysis material total, 19. Supernatant after dialysis, 20. Pellet after dialysis, 21. Filtrated protein.

Example 7

Figure 8:
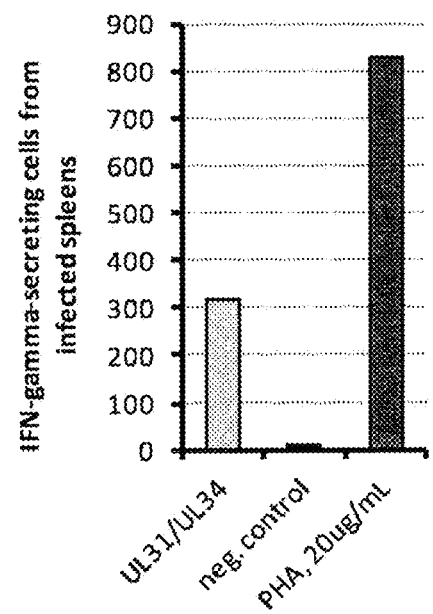
FIG. 8: UL31/UL34 dimer ELISPOT with infected guinea pigs

Splenocytes from HSV-2 infected and control guinea pigs ($1 \times 10^5$ cells) were mixed with 20 µg/mL of HSV-2 UL31/UL34 complex. Cells were then transferred onto ELISPOT anti-interferon gamma (IFN-γ) antibody-coated plates (Multiscreen HTS Plates; Millipore) and incubated for 20 h. Plates were thereafter developed according to standard ELISPOT protocols and the IFN-γ secreting cells were quantified as spots using an automated reader. Unstimulated cells and 20 µg/mL of PHA were used as negative and positive controls, respectively. Results are shown in FIG. 8.

Example 8

Figure 9:
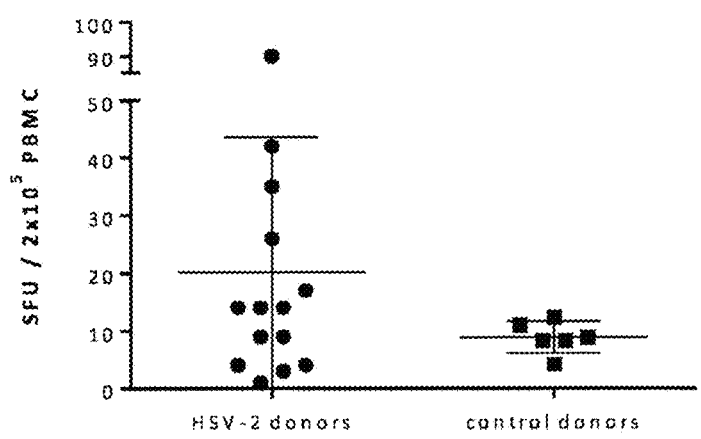
FIG. 9: UL31/UL34 dimer ELISPOT with patient PBMC

PBMC from fourteen HSV-2-infected and six uninfected individuals were thawed and left rest overnight. Cells were plated onto ELISPOT anti-interferon gamma (IFN-γ) antibody coated plates at $2 \times 10^5$ cells/well. Cells were subsequently stimulated with 5 µg/mL of HSV-2 UL31/UL34 complex for 48 h. Plates were thereafter developed according to manufacturer's instructions and the IFN-γ secreting cells were counted as spots with an automated reader. The background signal (generated from buffer-stimulated cells) was subtracted from each well and results were expressed as SFU (spot forming units) per $2 \times 10^5$ PBMC. Results are shown in FIG. 9. HSV-2 proteins UL31 and UL34 cannot be expressed as monomers, but only as dimers (personal observation, data not shown). Thus, responses of the UL31/UL34 complex and the respective monomers could not be compared, as shown for the UL48/UL49 and UL11/UL16/UL21 complexes (see FIGS. 10 and 12).

Example 9

Figure 10:
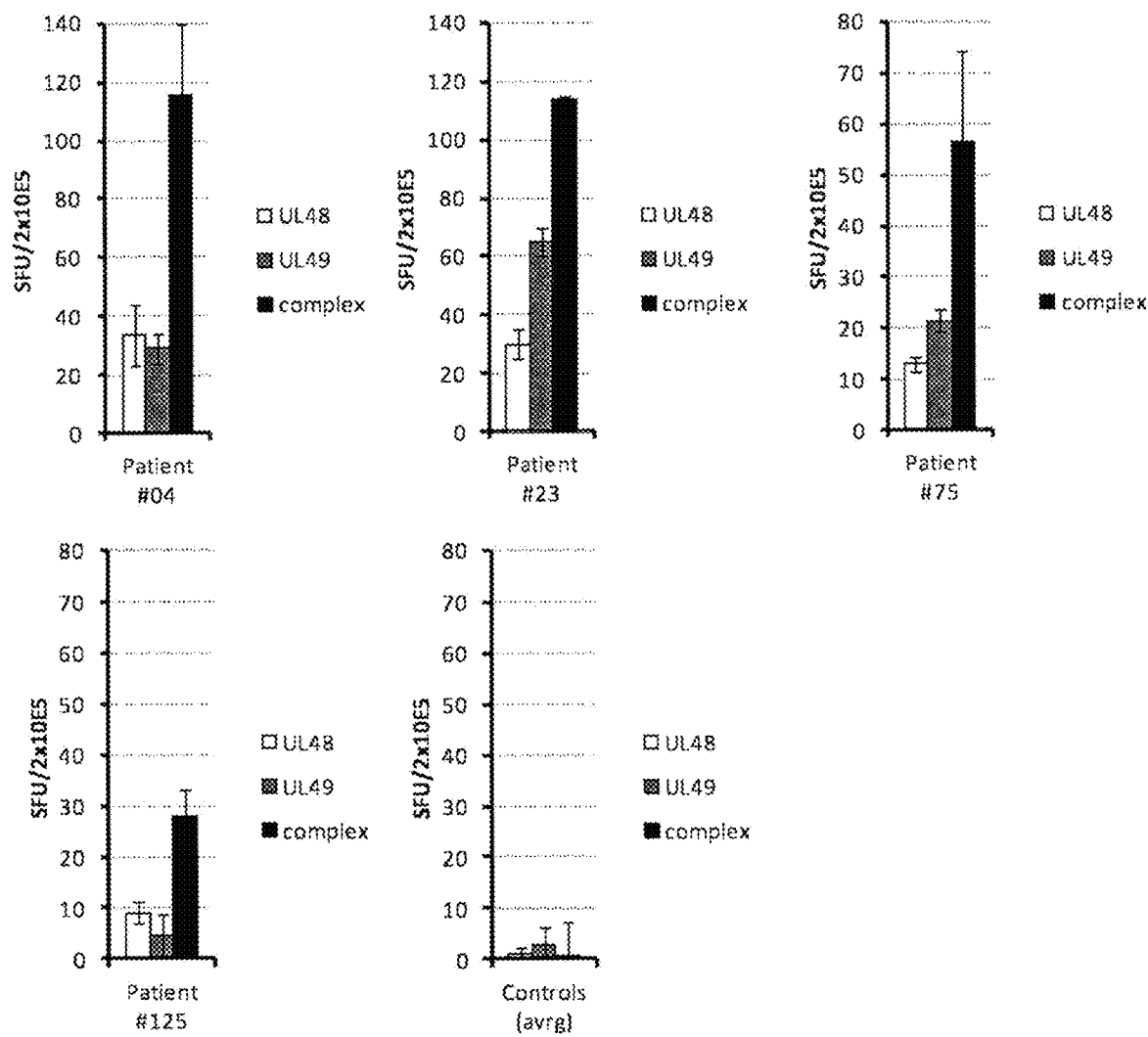
FIG. 10: UL48/UL49 dimer ELISPOT with patient PBMC

PBMC from four HSV-2-infected and two uninfected individuals were thawed and left rest overnight. Cells were plated onto ELISPOT anti-interferon gamma (IFN-γ) antibody coated plates at $2 \times 10^5$ cells/well. Cells were subsequently stimulated with 5 µg/mL of HSV-2 UL48/UL49 complex, or the respective monomers normalized to the amount of the single proteins in the complex, for 48 h. Plates were thereafter developed according to manufacturer's instructions and the IFN-γ secreting cells were counted as spots with an automated reader. The background signal (generated from buffer-stimulated cells) was subtracted from each well and results were expressed as SFU (spot forming units) per $2 \times 10^5$ PBMC. Results are shown in FIG. 10. The response of the uninfected individuals is shown here as an average value.

Example 10

Figure 11:
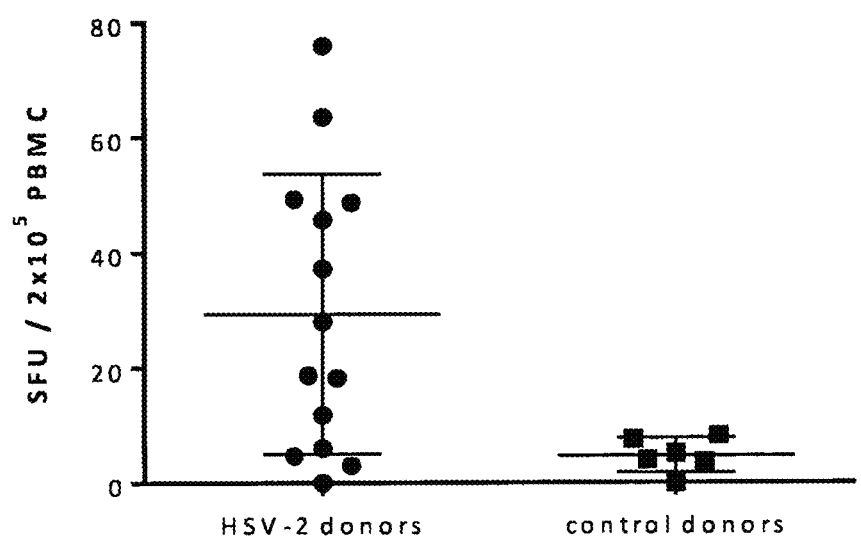
FIG. 11: UL48/UL49 dimer ELISPOT with patient PBMC

PBMC from fourteen HSV-2-infected and six uninfected individuals were thawed and left rest overnight. Cells were plated onto ELISPOT anti-interferon gamma (IFN-γ) antibody coated plates at 2×10⁵ cells/well. Cells were subsequently stimulated with 5 μg/mL of HSV-2 UL48/UL49 complex for 48 h. Plates were thereafter developed according to manufacturer's instructions and the IFN-γ secreting cells were counted as spots with an automated reader. The background signal (generated from buffer-stimulated cells) was subtracted from each well and results were expressed as SFU (spot forming units) per 2×10⁵ PBMC. Results are shown in FIG. 11.

Example 11

Figure 12:
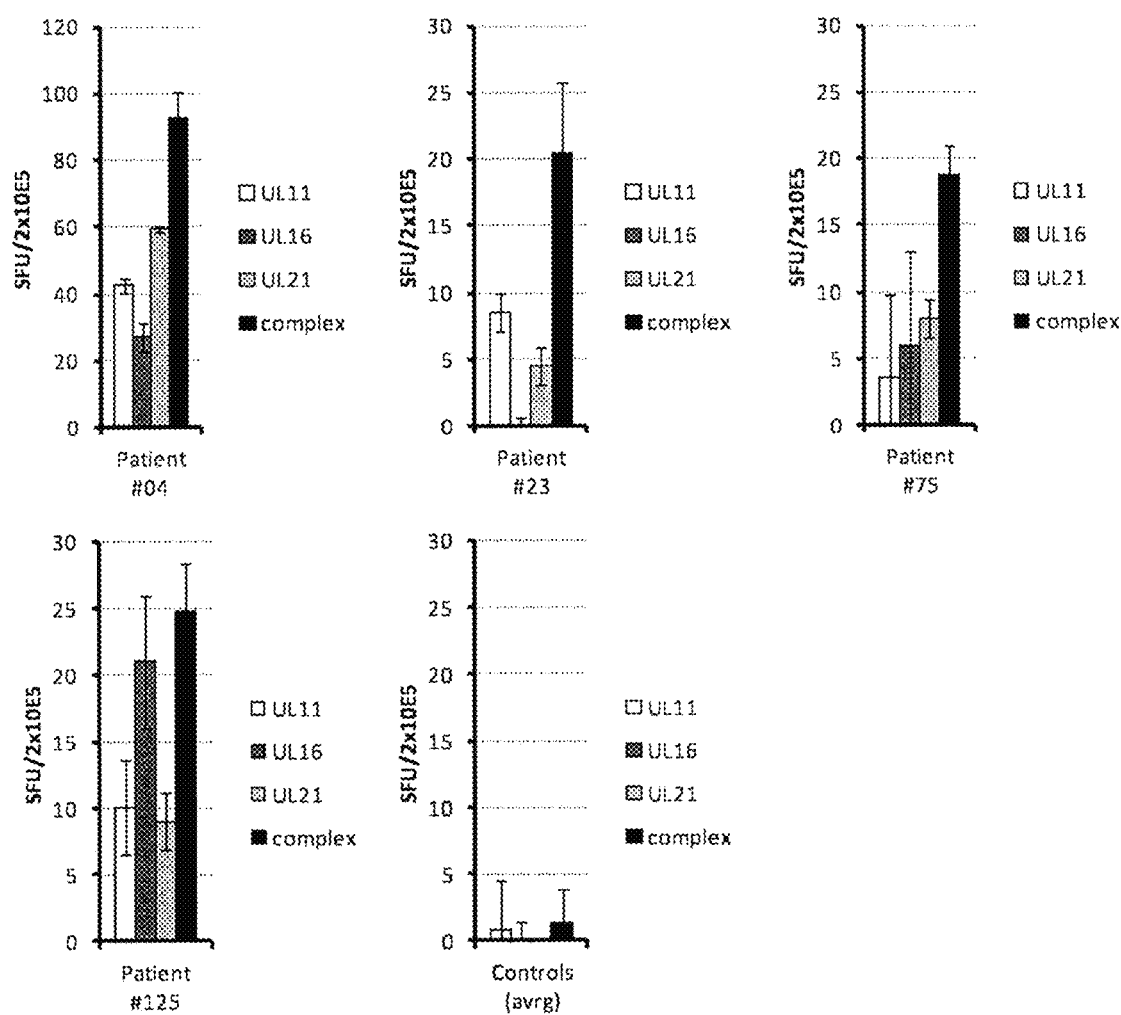
FIG. 12: UL11/UL16/UL21 trimer ELISPOT with patient PBMC

PBMC from four HSV-2-infected and two uninfected individuals were thawed and left rest overnight. Cells were plated onto ELISPOT anti-interferon gamma (IFN-γ) antibody coated plates at 2×10⁵ cells/well. Cells were subsequently stimulated with 5 μg/mL of HSV-2 UL11/UL16/UL21 complex, or the respective monomers normalized to the amount of the single proteins in the complex, for 48 h. Plates were thereafter developed according to manufacturer's instructions and the IFN-γ secreting cells were counted as spots with an automated reader. The background signal (generated from buffer-stimulated cells) was subtracted from each well and results were expressed as SFU (spot forming units) per 2×10⁵ PBMC. Results are shown in FIG. 12. The response of the uninfected individuals is shown here as an average value.

Example 12

Figure 13:
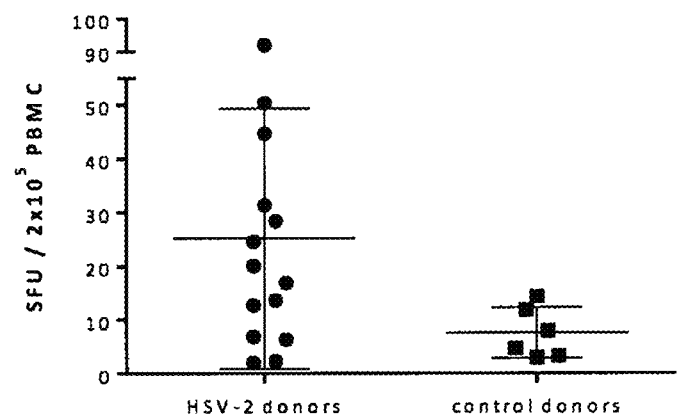
FIG. 13: UL11/UL16/UL21 trimer ELISPOT with patient PBMC

PBMC from fourteen HSV-2-infected and six uninfected individuals were thawed and left rest overnight. Cells were plated onto ELISPOT anti-interferon gamma (IFN-γ) antibody coated plates at 2×10⁵ cells/well. Cells were subsequently stimulated with 5 μg/mL of HSV-2 UL11/UL16/UL21 complex for 48 h. Plates were thereafter developed according to manufacturer's instructions and the IFN-γ secreting cells were counted as spots with an automated reader. The background signal (generated from buffer-stimulated cells) was subtracted from each well and results were expressed as SFU (spot forming units) per 2×10⁵ PBMC. Results are shown in FIG. 13.

Example 13

Figure 14:
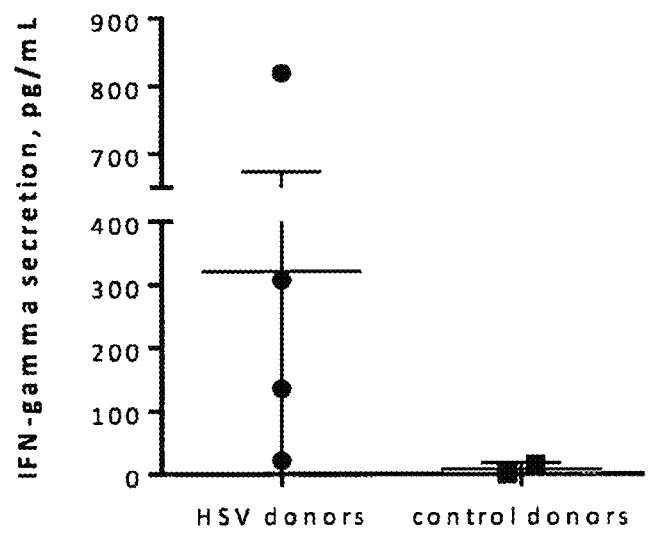
FIG. 14: UL31/UL34 dimer Luminex assay with patient PBMC

PBMC from four HSV-2-infected individuals and two uninfected individuals were thawed and left rest overnight. Cells were seeded onto plates at 5×10⁵ cells/well and subsequently stimulated with 5 μg/mL of HSV-2 UL31/UL34 complex for 48 h. Supernatants were thereafter collected and analyzed for the secretion of IFN-γ with a Luminex instrument. The background signal (generated from buffer-stimulated cells) was subtracted from each well and results were expressed as pg/ml. Results are shown in FIG. 14.

Example 14

Figure 15:
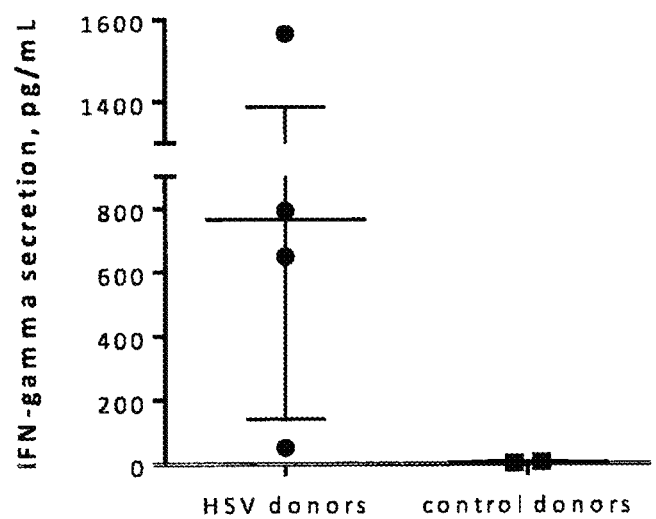
FIG. 15: UL48/UL49 dimer Luminex assay with patient PBMC

PBMC from four HSV-2-infected individuals and two uninfected individuals were thawed and left rest overnight. Cells were seeded onto plates at 5×10⁵ cells/well and subsequently stimulated with 5 μg/mL of HSV-2 UL48/UL49 complex for 48 h. Supernatants were thereafter collected and analyzed for the secretion of IFN-γ with a Luminex instrument. The background signal (generated from buffer-stimulated cells) was subtracted from each well and results were expressed as pg/ml. Results are shown in FIG. 15.

Example 15

Figure 16:
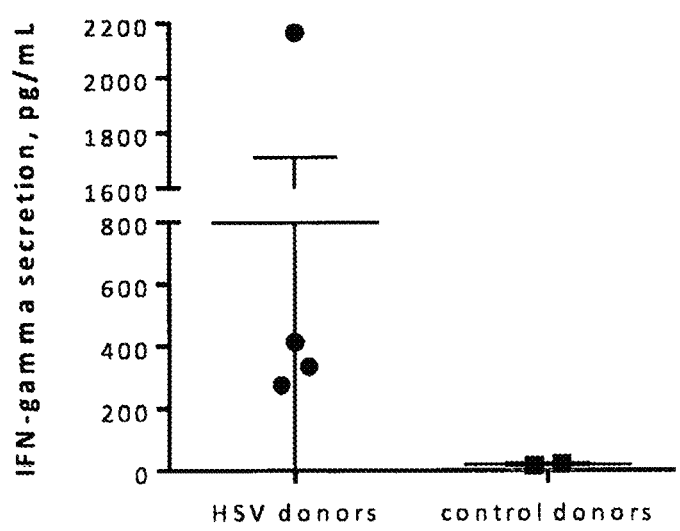
FIG. 16: UL11/UL16/UL21 trimer Luminex assay with patient PBMC

PBMC from four HSV-2-infected individuals and two uninfected individuals were thawed and left rest overnight. Cells were seeded onto plates at 5×10⁵ cells/well and subsequently stimulated with 5 μg/mL of HSV-2 UL11/UL16/UL21 complex for 48 h. Supernatants were thereafter collected and analyzed for the secretion of IFN-γ with a Luminex instrument. The background signal (generated from buffer-stimulated cells) was subtracted from each well and results were expressed as pg/ml. Results are shown in FIG. 16.

The invention claimed is:

1. A method for treating, reducing or ameliorating HSV-1 or HSV-2 infection or preventing symptoms or reactivation of HSV-1 or HSV-2, comprising the step of administering to a human subject in need thereof an effective amount of an immunogenic composition by injection or infusion, wherein the immunogenic composition comprises a single Herpes Simplex Virus (HSV) multimeric complex consisting of:
   (i) HSV polypeptides UL11, UL16 and UL21 and optionally HSV glycoprotein E (gE),
   (ii) HSV polypeptides UL48 and UL49 as a dimer, or
   (iii) HSV polypeptides UL31 and UL34 as a dimer.

2. The method of claim 1, wherein said HSV polypeptide UL11 comprises an amino acid sequence which is 75% or more identical to the amino acid sequence of SEQ ID NO: 1, wherein said HSV polypeptide UL11 is capable of eliciting an immune response when administered in the form of an immunogenic composition to a subject.

3. The method of claim 1, wherein said HSV polypeptide UL16 comprises an amino acid sequence which is 72% or more identical to the amino acid sequence of SEQ ID NO: 2, wherein said HSV polypeptide UL16 is capable of eliciting an immune response when administered in the form of an immunogenic composition to a subject.

4. The method of claim 1, wherein said HSV polypeptide UL21 comprises an amino acid sequence which is 80% or more identical to the amino acid sequence of SEQ ID NO: 3, wherein said HSV polypeptide UL21 is capable of eliciting an immune response when administered in the form of an immunogenic composition to a subject.

5. The method of claim 1, wherein said HSV polypeptide UL48 comprises an amino acid sequence which is 80% or more identical to the amino acid sequence of SEQ ID NO: 6, wherein said HSV polypeptide UL48 is capable of eliciting an immune response when administered in the form of an immunogenic composition to a subject.

6. The method of claim 1, wherein said HSV polypeptide UL49 comprises an amino acid sequence which is 62% or more identical to the amino acid sequence of SEQ ID NO: 7, wherein said HSV polypeptide UL49 is capable of eliciting an immune response when administered in the form of an immunogenic composition to a subject.

7. The method of claim 1, wherein said HSV polypeptide UL31 comprises an amino acid sequence which is 85% or more identical to the amino acid sequence of SEQ ID NO: 8, wherein said HSV polypeptide UL31 is capable of eliciting an immune response when administered in the form of an immunogenic composition to a subject.

8. The method of claim 1, wherein said HSV polypeptide UL34 comprises an amino acid sequence which is 70% or more identical to the amino acid sequence of SEQ ID NO: 9, wherein said HSV polypeptide UL34 is capable of eliciting an immune response when administered in the form of an immunogenic composition to a subject.

9. The method of claim 1, wherein said multimeric complex consists of HSV polypeptides UL11, UL16, UL21 and HSV gE.

10. The method of claim 9, wherein said HSV gE comprises an amino acid sequence which is 70% or more identical to the amino acid sequence of SEQ ID NO: 4, and wherein said HSV gE is capable of eliciting an immune response when administered in the form of an immunogenic composition to a subject.

11. The method of claim 9, wherein said HSV gE consists of the cytoplasmic domain of said HSV gE.

12. The method of claim 11, wherein said cytoplasmic domain of HSV gE comprises an amino acid sequence which is 80% or more identical to the amino acid sequence of SEQ ID NO: 5, and wherein said cytoplasmic domain of HSV gE is capable of eliciting an immune response when administered in the form of an immunogenic composition to a subject.

13. The method of claim 1, wherein said polypeptides are HSV-1 polypeptides.

14. The method of claim 1, wherein said polypeptides are HSV-2 polypeptides.

15. The method of claim 1, wherein said polypeptides are encoded by a nucleic acid.

16. The method of claim 1, wherein the immunogenic composition further comprises a pharmaceutically acceptable carrier or adjuvant.

17. The method of claim 1, wherein the method is for treating, reducing or ameliorating HSV-1 infection or preventing symptoms or reactivation of HSV-1.

18. The method of claim 1, wherein the method is for treating, reducing or ameliorating HSV-2 infection or preventing symptoms or reactivation of HSV-2.

19. A method for producing an immunogenic composition for injection or infusion, comprising
- (i) culturing an isolated host cell comprising a recombinant vector that comprises a polynucleotide encoding an HSV complex consisting of:
  - (a) UL11, UL16 and UL21, and optionally gE or the cytoplasmic domain of gE,
  - (b) UL48 and UL49, or
  - (c) UL31 and UL34;
- (ii) obtaining an isolated multimeric complex consisting of
  - (a) UL11, UL16, UL21 and optionally gE or the cytoplasmic domain of gE;
  - (b) UL48 and UL49 as a dimer; or
  - (c) UL31 and UL34 dimer; and
- (iii) admixing said isolated multimeric complex with a pharmaceutically acceptable carrier or adjuvant for injection or infusion.

* * * * *

SEQUENCE LISTING

```
<160> NUMBER OF SEQ ID NOS: 10

<210> SEQ ID NO 1
<211> LENGTH: 96
<212> TYPE: PRT
<213> ORGANISM: Artificial Sequence
<220> FEATURE:
<223> OTHER INFORMATION: UL11 protein of HSV-2

<400> SEQUENCE: 1

Met Gly Leu Ala Phe Ser Gly Ala Arg Pro Cys Cys Arg His Asn
1               5                   10                  15

Val Ile Ile Thr Asp Gly Gly Glu Val Val Ser Leu Thr Ala His Glu
                20                  25                  30

Phe Asp Val Val Asp Ile Glu Ser Glu Glu Gly Asn Phe Tyr Val
            35                  40                  45

Pro Pro Asp Met Arg Val Val Thr Arg Ala Pro Gly Pro Gln Tyr Arg
        50                  55                  60

Arg Ala Ser Asp Pro Pro Ser Arg His Thr Arg Arg Arg Asp Pro Asp
65                  70                  75                  80
```

```
Val Ala Arg Pro Pro Ala Thr Leu Thr Pro Pro Leu Ser Asp Ser Glu
                85                  90                  95
```

<210> SEQ ID NO 2
<211> LENGTH: 372
<212> TYPE: PRT
<213> ORGANISM: Artificial Sequence
<220> FEATURE:
<223> OTHER INFORMATION: UL16 protein of HSV-2

<400> SEQUENCE: 2

```
Met Ala Gln Arg Ala Leu Trp Arg Pro Gln Ala Thr Pro Gly Pro Pro
1               5                   10                  15

Gly Ala Ala Ala Pro Pro Gly His Arg Gly Ala Pro Pro Asp Ala Arg
                20                  25                  30

Ala Pro Asp Pro Gly Pro Glu Ala Asp Leu Val Ala Arg Ile Ala Asn
            35                  40                  45

Ser Val Phe Val Trp Arg Val Val Arg Gly Asp Glu Arg Leu Lys Ile
        50                  55                  60

Phe Arg Cys Leu Thr Val Leu Thr Glu Pro Leu Cys Gln Val Ala Leu
65                  70                  75                  80

Pro Asp Pro Asp Pro Glu Arg Ala Leu Phe Cys Glu Ile Phe Leu Tyr
                85                  90                  95

Leu Thr Arg Pro Lys Ala Leu Arg Leu Pro Ser Asn Thr Phe Phe Ala
                100                 105                 110

Ile Phe Phe Phe Asn Arg Glu Arg Arg Tyr Cys Ala Thr Val His Leu
            115                 120                 125

Arg Ser Val Thr His Pro Arg Thr Pro Leu Leu Cys Thr Leu Ala Phe
        130                 135                 140

Gly His Leu Glu Ala Ala Ser Pro Pro Glu Glu Thr Pro Asp Pro Ala
145                 150                 155                 160

Ala Glu Gln Leu Ala Asp Glu Pro Val Ala His Glu Leu Asp Gly Ala
                165                 170                 175

Tyr Leu Val Pro Thr Glu Pro Pro Asn Pro Gly Ala Cys Cys Ala
                180                 185                 190

Leu Gly Pro Gly Ala Trp Trp His Leu Pro Gly Gly Arg Ile Tyr Cys
            195                 200                 205

Trp Ala Met Asp Asp Leu Gly Ser Leu Cys Pro Pro Gly Ser Arg
210                 215                 220

Ala Arg His Leu Gly Trp Leu Leu Ser Arg Ile Thr Asp Pro Pro Gly
225                 230                 235                 240

Gly Gly Gly Ala Cys Ala Pro Thr Ala His Ile Asp Ser Ala Asn Ala
                245                 250                 255

Leu Trp Arg Ala Pro Ala Val Ala Glu Ala Cys Pro Cys Val Ala Pro
                260                 265                 270

Cys Met Trp Ser Asn Met Ala Gln Arg Thr Leu Ala Val Arg Gly Asp
            275                 280                 285

Ala Ser Leu Cys Gln Leu Leu Phe Gly His Pro Val Asp Ala Val Ile
        290                 295                 300

Leu Arg Gln Ala Thr Arg Arg Pro Arg Ile Thr Ala His Leu His Glu
305                 310                 315                 320

Val Val Val Gly Arg Asp Gly Ala Glu Ser Val Ile Arg Pro Thr Ser
                325                 330                 335

Ala Gly Trp Arg Leu Cys Val Leu Ser Ser Tyr Thr Ser Arg Leu Phe
                340                 345                 350
```

```
Ala Thr Ser Cys Pro Ala Val Ala Arg Ala Val Ala Arg Ala Ser Ser
        355                 360                 365

Ser Asp Tyr Lys
    370

<210> SEQ ID NO 3
<211> LENGTH: 532
<212> TYPE: PRT
<213> ORGANISM: Artificial Sequence
<220> FEATURE:
<223> OTHER INFORMATION: UL21 protein of HSV-2

<400> SEQUENCE: 3

Met Glu Leu Ser Tyr Ala Thr Thr Leu His His Arg Asp Val Val Phe
1               5                   10                  15

Tyr Val Thr Ala Asp Arg Asn Arg Ala Tyr Phe Val Cys Gly Gly Ser
            20                  25                  30

Val Tyr Ser Val Gly Arg Pro Arg Asp Ser Gln Pro Gly Glu Ile Ala
        35                  40                  45

Lys Phe Gly Leu Val Val Arg Gly Thr Gly Pro Lys Asp Arg Met Val
    50                  55                  60

Ala Asn Tyr Val Arg Ser Glu Leu Arg Gln Arg Gly Leu Arg Asp Val
65                  70                  75                  80

Arg Pro Val Gly Glu Asp Glu Val Phe Leu Asp Ser Val Cys Leu Leu
                85                  90                  95

Asn Pro Asn Val Ser Ser Glu Arg Asp Val Ile Asn Thr Asn Asp Val
            100                 105                 110

Glu Val Leu Asp Glu Cys Leu Ala Glu Tyr Cys Thr Ser Leu Arg Thr
        115                 120                 125

Ser Pro Gly Val Leu Val Thr Gly Val Arg Val Arg Ala Arg Asp Arg
    130                 135                 140

Val Ile Glu Leu Phe Glu His Pro Ala Ile Val Asn Ile Ser Ser Arg
145                 150                 155                 160

Phe Ala Tyr Thr Pro Ser Pro Tyr Val Phe Ala Leu Ala Gln Ala His
                165                 170                 175

Leu Pro Arg Leu Pro Ser Ser Leu Glu Pro Leu Val Ser Gly Leu Phe
            180                 185                 190

Asp Gly Ile Pro Ala Pro Arg Gln Pro Leu Asp Ala Arg Asp Arg Arg
        195                 200                 205

Thr Asp Val Val Ile Thr Gly Thr Arg Ala Pro Arg Pro Met Ala Gly
    210                 215                 220

Thr Gly Ala Gly Gly Ala Gly Ala Lys Arg Ala Thr Val Ser Glu Phe
225                 230                 235                 240

Val Gln Val Lys His Ile Asp Arg Val Val Ser Pro Ser Val Ser Ser
                245                 250                 255

Ala Pro Pro Ser Ala Pro Asp Ala Ser Leu Pro Pro Gly Leu
            260                 265                 270

Gln Glu Ala Ala Pro Pro Gly Pro Leu Arg Glu Leu Trp Trp Val
        275                 280                 285

Phe Tyr Ala Gly Asp Arg Ala Leu Glu Glu Pro His Ala Glu Ser Gly
    290                 295                 300

Leu Thr Arg Glu Glu Val Arg Ala Val His Gly Phe Arg Glu Gln Ala
305                 310                 315                 320

Trp Lys Leu Phe Gly Ser Val Gly Ala Pro Arg Ala Phe Leu Gly Ala
                325                 330                 335
```

```
Ala Leu Ala Leu Ser Pro Thr Gln Lys Leu Ala Val Tyr Tyr Tyr Leu
            340                 345                 350

Ile His Arg Glu Arg Met Ser Pro Phe Pro Ala Leu Val Arg Leu
        355                 360                 365

Val Gly Arg Tyr Ile Gln Arg His Gly Leu Tyr Val Pro Ala Pro Asp
    370                 375                 380

Glu Pro Thr Leu Ala Asp Ala Met Asn Gly Leu Phe Arg Asp Ala Leu
385                 390                 395                 400

Ala Ala Gly Thr Val Ala Glu Gln Leu Leu Met Phe Asp Leu Leu Pro
                405                 410                 415

Pro Lys Asp Val Pro Val Gly Ser Asp Ala Arg Ala Asp Ser Ala Ala
            420                 425                 430

Leu Leu Arg Phe Val Asp Ser Gln Arg Leu Thr Pro Gly Gly Ser Val
        435                 440                 445

Ser Pro Glu His Val Met Tyr Leu Gly Ala Phe Leu Gly Val Leu Tyr
    450                 455                 460

Ala Gly His Gly Arg Leu Ala Ala Ala Thr His Thr Ala Arg Leu Thr
465                 470                 475                 480

Gly Val Thr Ser Leu Val Leu Thr Val Gly Asp Val Asp Arg Met Ser
                485                 490                 495

Ala Phe Asp Arg Gly Pro Ala Gly Ala Ala Gly Arg Thr Arg Thr Ala
            500                 505                 510

Gly Tyr Leu Asp Ala Leu Leu Thr Val Cys Leu Ala Arg Ala Gln His
        515                 520                 525

Gly Gln Ser Val
    530

<210> SEQ ID NO 4
<211> LENGTH: 548
<212> TYPE: PRT
<213> ORGANISM: Artificial Sequence
<220> FEATURE:
<223> OTHER INFORMATION: gE protein of HSV-2

<400> SEQUENCE: 4

Met Ala Arg Gly Ala Gly Leu Val Phe Phe Val Gly Val Trp Val Val
1               5                   10                  15

Ser Cys Leu Ala Ala Ala Pro Arg Thr Ser Trp Lys Arg Val Thr Ser
            20                  25                  30

Gly Glu Asp Val Val Leu Leu Pro Ala Pro Ala Gly Pro Glu Glu Arg
        35                  40                  45

Thr Arg Ala His Lys Leu Leu Trp Ala Ala Glu Pro Leu Asp Ala Cys
    50                  55                  60

Gly Pro Leu Arg Pro Ser Trp Val Ala Leu Trp Pro Pro Arg Arg Val
65                  70                  75                  80

Leu Glu Thr Val Val Asp Ala Ala Cys Met Arg Ala Pro Glu Pro Leu
                85                  90                  95

Ala Ile Ala Tyr Ser Pro Pro Phe Pro Ala Gly Asp Glu Gly Leu Tyr
            100                 105                 110

Ser Glu Leu Ala Trp Arg Asp Arg Val Ala Val Asn Glu Ser Leu
        115                 120                 125

Val Ile Tyr Gly Ala Leu Glu Thr Asp Ser Gly Leu Tyr Thr Leu Ser
    130                 135                 140

Val Val Gly Leu Ser Asp Glu Ala Arg Gln Val Ala Ser Val Val Leu
145                 150                 155                 160
```

```
Val Val Glu Pro Ala Pro Val Pro Thr Pro Thr Pro Asp Asp Tyr Asp
                165                 170                 175

Glu Glu Asp Asp Ala Gly Val Ser Glu Arg Thr Pro Val Ser Val Pro
            180                 185                 190

Pro Pro Thr Pro Pro Arg Arg Pro Pro Val Ala Pro Pro Thr His Pro
        195                 200                 205

Arg Val Ile Pro Glu Val Ser His Val Arg Gly Val Thr Val His Met
    210                 215                 220

Glu Thr Pro Glu Ala Ile Leu Phe Ala Pro Gly Glu Thr Phe Gly Thr
225                 230                 235                 240

Asn Val Ser Ile His Ala Ile Ala His Asp Asp Gly Pro Tyr Ala Met
                245                 250                 255

Asp Val Val Trp Met Arg Phe Asp Val Pro Ser Ser Cys Ala Glu Met
                260                 265                 270

Arg Ile Tyr Glu Ala Cys Leu Tyr His Pro Gln Leu Pro Glu Cys Leu
            275                 280                 285

Ser Pro Ala Asp Ala Pro Cys Ala Val Ser Ser Trp Ala Tyr Arg Leu
        290                 295                 300

Ala Val Arg Ser Tyr Ala Gly Cys Ser Arg Thr Thr Pro Pro Pro Arg
305                 310                 315                 320

Cys Phe Ala Glu Ala Arg Met Glu Pro Val Pro Gly Leu Ala Trp Leu
                325                 330                 335

Ala Ser Thr Val Asn Leu Glu Phe Gln His Ala Ser Pro Gln His Ala
                340                 345                 350

Gly Leu Tyr Leu Cys Val Val Tyr Val Asp Asp His Ile His Ala Trp
            355                 360                 365

Gly His Met Thr Ile Ser Thr Ala Ala Gln Tyr Arg Asn Ala Val Val
        370                 375                 380

Glu Gln His Leu Pro Gln Arg Gln Pro Glu Pro Val Glu Pro Thr Arg
385                 390                 395                 400

Pro His Val Arg Ala Pro Pro Ala Pro Ser Ala Arg Gly Pro Leu
                405                 410                 415

Arg Leu Gly Ala Val Leu Gly Ala Ala Leu Leu Leu Ala Ala Leu Gly
            420                 425                 430

Leu Ser Ala Trp Ala Cys Met Thr Cys Trp Arg Arg Ser Trp Arg
        435                 440                 445

Ala Val Lys Ser Arg Ala Ser Ala Thr Gly Pro Thr Tyr Ile Arg Val
    450                 455                 460

Ala Asp Ser Glu Leu Tyr Ala Asp Trp Ser Ser Asp Ser Glu Gly Glu
465                 470                 475                 480

Arg Asp Gly Ser Leu Trp Gln Asp Pro Pro Glu Arg Pro Asp Ser Pro
                485                 490                 495

Ser Thr Asn Gly Ser Gly Phe Glu Ile Leu Ser Pro Thr Ala Pro Ser
                500                 505                 510

Val Tyr Pro His Ser Glu Gly Arg Lys Ser Arg Arg Pro Leu Thr Thr
            515                 520                 525

Phe Gly Ser Gly Ser Pro Gly Arg Arg His Ser Gln Ala Ser Tyr Ser
        530                 535                 540

Ser Val Leu Trp
545

<210> SEQ ID NO 5
<211> LENGTH: 106
```

```
<212> TYPE: PRT
<213> ORGANISM: Artificial Sequence
<220> FEATURE:
<223> OTHER INFORMATION: Cytoplasmic tail of gE protein of HSV-2

<400> SEQUENCE: 5

Arg Arg Arg Ser Trp Arg Ala Val Lys Ser Arg Ala Ser Ala Thr Gly
1               5                   10                  15

Pro Thr Tyr Ile Arg Val Ala Asp Ser Glu Leu Tyr Ala Asp Trp Ser
            20                  25                  30

Ser Asp Ser Glu Gly Glu Arg Asp Gly Ser Leu Trp Gln Asp Pro Pro
        35                  40                  45

Glu Arg Pro Asp Ser Pro Ser Thr Asn Gly Ser Gly Phe Glu Ile Leu
    50                  55                  60

Ser Pro Thr Ala Pro Ser Val Tyr Pro His Ser Glu Gly Arg Lys Ser
65                  70                  75                  80

Arg Arg Pro Leu Thr Thr Phe Gly Ser Gly Ser Pro Gly Arg Arg His
                85                  90                  95

Ser Gln Ala Ser Tyr Ser Ser Val Leu Trp
            100                 105

<210> SEQ ID NO 6
<211> LENGTH: 490
<212> TYPE: PRT
<213> ORGANISM: Artificial Sequence
<220> FEATURE:
<223> OTHER INFORMATION: UL48 protein of HSV-2

<400> SEQUENCE: 6

Met Asp Leu Leu Val Asp Asp Leu Phe Ala Asp Ala Asp Gly Val Ser
1               5                   10                  15

Pro Pro Pro Pro Arg Pro Ala Gly Gly Pro Lys Asn Thr Pro Ala Ala
            20                  25                  30

Pro Pro Leu Tyr Ala Thr Gly Arg Leu Ser Gln Ala Gln Leu Met Pro
        35                  40                  45

Ser Pro Pro Met Pro Val Pro Pro Ala Ala Leu Phe Asn Arg Leu Leu
    50                  55                  60

Asp Asp Leu Gly Phe Ser Ala Gly Pro Ala Leu Cys Thr Met Leu Asp
65                  70                  75                  80

Thr Trp Asn Glu Asp Leu Phe Ser Gly Phe Pro Thr Asn Ala Asp Met
                85                  90                  95

Tyr Arg Glu Cys Lys Phe Leu Ser Thr Leu Pro Ser Asp Val Ile Asp
            100                 105                 110

Trp Gly Asp Ala His Val Pro Glu Arg Ser Pro Ile Asp Ile Arg Ala
        115                 120                 125

His Gly Asp Val Ala Phe Pro Thr Leu Pro Ala Thr Arg Asp Glu Leu
    130                 135                 140

Pro Ser Tyr Tyr Glu Ala Met Ala Gln Phe Phe Arg Gly Glu Leu Arg
145                 150                 155                 160

Ala Arg Glu Glu Ser Tyr Arg Thr Val Leu Ala Asn Phe Cys Ser Ala
                165                 170                 175

Leu Tyr Arg Tyr Leu Arg Ala Ser Val Arg Gln Leu His Arg Gln Ala
            180                 185                 190

His Met Arg Gly Arg Asn Arg Asp Leu Arg Glu Met Leu Arg Thr Thr
        195                 200                 205

Ile Ala Asp Arg Tyr Tyr Arg Glu Thr Ala Arg Leu Ala Arg Val Leu
    210                 215                 220
```

Phe Leu His Leu Tyr Leu Phe Leu Ser Arg Glu Ile Leu Trp Ala Ala
225                 230                 235                 240

Tyr Ala Glu Gln Met Met Arg Pro Asp Leu Phe Asp Gly Leu Cys Cys
            245                 250                 255

Asp Leu Glu Ser Trp Arg Gln Leu Ala Cys Leu Phe Gln Pro Leu Met
        260                 265                 270

Phe Ile Asn Gly Ser Leu Thr Val Arg Gly Val Pro Val Glu Ala Arg
    275                 280                 285

Arg Leu Arg Glu Leu Asn His Ile Arg Glu His Leu Asn Leu Pro Leu
290                 295                 300

Val Arg Ser Ala Ala Glu Glu Pro Gly Ala Pro Leu Thr Thr Pro
305                 310                 315                 320

Pro Val Leu Gln Gly Asn Gln Ala Arg Ser Gly Tyr Phe Met Leu
            325                 330                 335

Leu Ile Arg Ala Lys Leu Asp Ser Tyr Ser Ser Val Ala Thr Ser Glu
        340                 345                 350

Gly Glu Ser Val Met Arg Glu His Ala Tyr Ser Arg Gly Arg Thr Arg
    355                 360                 365

Asn Asn Tyr Gly Ser Thr Ile Glu Gly Leu Leu Asp Leu Pro Asp Asp
370                 375                 380

Asp Asp Ala Pro Ala Glu Ala Gly Leu Val Ala Pro Arg Met Ser Phe
385                 390                 395                 400

Leu Ser Ala Gly Gln Arg Pro Arg Arg Leu Ser Thr Thr Ala Pro Ile
            405                 410                 415

Thr Asp Val Ser Leu Gly Asp Glu Leu Arg Leu Asp Gly Glu Glu Val
        420                 425                 430

Asp Met Thr Pro Ala Asp Ala Leu Asp Asp Phe Asp Leu Glu Met Leu
    435                 440                 445

Gly Asp Val Glu Ser Pro Ser Pro Gly Met Thr His Asp Pro Val Ser
450                 455                 460

Tyr Gly Ala Leu Asp Val Asp Asp Phe Glu Phe Glu Gln Met Phe Thr
465                 470                 475                 480

Asp Ala Met Gly Ile Asp Asp Phe Gly Gly
            485                 490

<210> SEQ ID NO 7
<211> LENGTH: 302
<212> TYPE: PRT
<213> ORGANISM: Artificial Sequence
<220> FEATURE:
<223> OTHER INFORMATION: UL49 protein of HSV-2

<400> SEQUENCE: 7

Met Thr Ser Arg Arg Ser Val Lys Ser Cys Pro Arg Glu Ala Pro Arg
1               5                   10                  15

Gly Thr His Glu Glu Leu Tyr Tyr Gly Pro Val Ser Pro Ala Asp Pro
            20                  25                  30

Glu Ser Pro Arg Asp Asp Phe Arg Arg Gly Ala Gly Pro Met Arg Ala
        35                  40                  45

Arg Pro Arg Gly Glu Val Arg Phe Leu His Tyr Asp Glu Ala Gly Tyr
    50                  55                  60

Ala Leu Tyr Arg Asp Ser Ser Ser Glu Asp Asn Asp Glu Ser Arg
65                  70                  75                  80

Asp Thr Ala Arg Pro Arg Arg Ser Ala Ser Val Ala Gly Ser His Gly
            85                  90                  95

```
Pro Gly Pro Ala Arg Ala Pro Pro Pro Gly Gly Pro Val Gly Ala
            100                 105                 110

Gly Gly Arg Ser His Ala Pro Pro Ala Arg Thr Pro Lys Met Thr Arg
        115                 120                 125

Gly Ala Pro Lys Ala Pro Ala Thr Pro Ala Thr Asp Pro Ala Arg Gly
130                 135                 140

Arg Arg Pro Ala Gln Ala Asp Ser Ala Val Leu Leu Asp Ala Pro Ala
145                 150                 155                 160

Pro Thr Ala Ser Gly Arg Thr Lys Thr Pro Ala Gln Gly Leu Ala Lys
                165                 170                 175

Lys Leu His Phe Ser Thr Ala Pro Pro Ser Pro Thr Ala Pro Trp Thr
            180                 185                 190

Pro Arg Val Ala Gly Phe Asn Lys Arg Val Phe Cys Ala Ala Val Gly
        195                 200                 205

Arg Leu Ala Ala Thr His Ala Arg Leu Ala Ala Val Gln Leu Trp Asp
    210                 215                 220

Met Ser Arg Pro His Thr Asp Glu Asp Leu Asn Glu Leu Leu Asp Leu
225                 230                 235                 240

Thr Thr Ile Arg Val Thr Val Cys Glu Gly Lys Asn Leu Leu Gln Arg
                245                 250                 255

Ala Asn Glu Leu Val Asn Pro Asp Ala Ala Gln Asp Val Asp Ala Thr
            260                 265                 270

Ala Ala Ala Arg Gly Arg Pro Ala Gly Arg Ala Ala Thr Ala Arg
        275                 280                 285

Ala Pro Ala Arg Ser Ala Ser Arg Pro Arg Pro Leu Glu
    290                 295                 300

<210> SEQ ID NO 8
<211> LENGTH: 305
<212> TYPE: PRT
<213> ORGANISM: Artificial Sequence
<220> FEATURE:
<223> OTHER INFORMATION: UL31 protein of HSV-2

<400> SEQUENCE: 8

Met Tyr Asp Ile Ala Pro Arg Arg Ser Gly Ser Arg Pro Gly Pro Gly
1               5                   10                  15

Arg Asp Lys Thr Arg Arg Ser Arg Phe Ser Ala Ala Gly Asn Pro
            20                  25                  30

Gly Val Glu Arg Arg Ala Ser Arg Lys Ser Leu Pro Ser His Ala Arg
        35                  40                  45

Arg Leu Glu Leu Cys Leu His Glu Arg Arg Tyr Arg Gly Phe Phe
50                  55                  60

Ala Ala Leu Ala Gln Thr Pro Ser Glu Glu Ile Ala Ile Val Arg Ser
65                  70                  75                  80

Leu Ser Val Pro Leu Val Lys Thr Thr Pro Val Ser Leu Pro Phe Ser
                85                  90                  95

Leu Asp Gln Thr Val Ala Asp Asn Cys Leu Thr Leu Ser Gly Met Gly
            100                 105                 110

Tyr Tyr Leu Gly Ile Gly Gly Cys Cys Pro Ala Cys Ser Ala Gly Asp
        115                 120                 125

Gly Arg Leu Ala Thr Val Ser Arg Glu Ala Leu Ile Leu Ala Phe Val
    130                 135                 140

Gln Gln Ile Asn Thr Ile Phe Glu His Arg Thr Phe Leu Ala Ser Leu
145                 150                 155                 160
```

Val Val Leu Ala Asp Arg His Ser Thr Pro Leu Gln Asp Leu Leu Ala
              165                 170                 175

Asp Thr Leu Gly Gln Pro Glu Leu Phe Phe Val His Thr Ile Leu Arg
              180                 185                 190

Gly Gly Gly Ala Cys Asp Pro Arg Phe Leu Phe Tyr Pro Asp Pro Thr
              195                 200                 205

Tyr Gly Gly His Met Leu Tyr Val Ile Phe Pro Gly Thr Ser Ala His
          210                 215                 220

Leu His Tyr Arg Leu Ile Asp Arg Met Leu Thr Ala Cys Pro Gly Tyr
225                 230                 235                 240

Arg Phe Ala Ala His Val Trp Gln Ser Thr Phe Val Leu Val Val Arg
              245                 250                 255

Arg Asn Ala Glu Lys Pro Ala Asp Ala Glu Ile Pro Thr Val Ser Ala
              260                 265                 270

Ala Asp Ile Tyr Cys Lys Met Arg Asp Ile Ser Phe Asp Gly Gly Leu
              275                 280                 285

Met Leu Glu Tyr Gln Arg Leu Tyr Ala Thr Phe Asp Glu Phe Pro Pro
              290                 295                 300

Pro
305

<210> SEQ ID NO 9
<211> LENGTH: 250
<212> TYPE: PRT
<213> ORGANISM: Artificial Sequence
<220> FEATURE:
<223> OTHER INFORMATION: UL34 protein of HSV-2

<400> SEQUENCE: 9

Met Ala Gly Met Gly Lys Pro Tyr Gly Gly Arg Pro Gly Asp Ala Phe
1               5                   10                  15

Glu Gly Leu Val Gln Arg Ile Arg Leu Ile Val Pro Thr Thr Leu Arg
              20                  25                  30

Gly Gly Gly Gly Glu Ser Gly Pro Tyr Ser Pro Ser Asn Pro Pro Ser
          35                  40                  45

Arg Cys Ala Phe Gln Phe His Gly Gln Asp Gly Ser Asp Glu Ala Phe
50                  55                  60

Pro Ile Glu Tyr Val Leu Arg Leu Met Asn Asp Trp Ala Asp Val Pro
65                  70                  75                  80

Cys Asn Pro Tyr Leu Arg Val Gln Asn Thr Gly Val Ser Val Leu Phe
              85                  90                  95

Gln Gly Phe Phe Asn Arg Pro His Gly Ala Pro Gly Gly Ala Ile Thr
              100                 105                 110

Ala Glu Gln Thr Asn Val Ile Leu His Ser Thr Glu Thr Thr Gly Leu
              115                 120                 125

Ser Leu Gly Asp Leu Asp Asp Val Lys Gly Arg Leu Gly Leu Asp Ala
          130                 135                 140

Arg Pro Met Met Ala Ser Met Trp Ile Ser Cys Phe Val Arg Met Pro
145                 150                 155                 160

Arg Val Gln Leu Ala Phe Arg Phe Met Gly Pro Glu Asp Ala Val Arg
              165                 170                 175

Thr Arg Arg Ile Leu Cys Arg Ala Ala Glu Gln Ala Leu Ala Arg Arg
              180                 185                 190

Arg Arg Ser Arg Arg Ser Gln Asp Asp Tyr Gly Ala Val Ala Val Ala
          195                 200                 205

```
Ala Ala His His Ser Ser Gly Ala Pro Gly Pro Gly Val Ala Ala Ser
        210                 215                 220

Gly Pro Pro Ala Pro Pro Gly Arg Gly Pro Ala Arg Pro Trp His Gln
225                 230                 235                 240

Ala Val Gln Leu Phe Arg Ala Pro Arg Pro
                245                 250

<210> SEQ ID NO 10
<211> LENGTH: 22
<212> TYPE: PRT
<213> ORGANISM: Artificial Sequence
<220> FEATURE:
<223> OTHER INFORMATION: Polypeptid linker and 8 His-tag

<400> SEQUENCE: 10

Gly Ala Gly Ser Gly Gly Gly Gly Ser Gly Gly Gly Gly Ser His His
1               5                   10                  15

His His His His His His
            20
```

UNITED STATES PATENT AND TRADEMARK OFFICE
CERTIFICATE OF CORRECTION

PATENT NO. : 11,058,765 B2
APPLICATION NO. : 16/084766
DATED : July 13, 2021
INVENTOR(S) : Garyfalia Stergiou et al.

Page 1 of 1

It is certified that error appears in the above-identified patent and that said Letters Patent is hereby corrected as shown below:

In the Claims

Column 43, Claim 19, Line 18:
"and UL34 dimer; and" should read: -- and UL34 as a dimer; and --.

Signed and Sealed this
Twelfth Day of July, 2022

Katherine Kelly Vidal
*Director of the United States Patent and Trademark Office*